(12) United States Patent
Azorsa et al.

(10) Patent No.: US 9,193,785 B2
(45) Date of Patent: Nov. 24, 2015

(54) HYBRIDOMA CLONES AND MONOCLONAL ANTIBODIES TO ING4

(71) Applicant: THE TRANSLATIONAL GENOMICS RESEARCH INSTITUTE, Phoenix, AZ (US)

(72) Inventors: David O. Azorsa, Phoenix, AZ (US); Suwon Kim, Phoenix, AZ (US)

(73) Assignees: The Translational Genomics Research Institute, Phoenix, AZ (US); The Arizona Board of Regents on Behalf of the University of Arizona, Tuscon, AZ (US)

(*) Notice: Subject to any disclaimer, the term of this patent is extended or adjusted under 35 U.S.C. 154(b) by 0 days.

(21) Appl. No.: 14/059,792

(22) Filed: Oct. 22, 2013

(65) Prior Publication Data

US 2014/0113834 A1 Apr. 24, 2014

Related U.S. Application Data

(60) Provisional application No. 61/718,177, filed on Oct. 24, 2012.

(51) Int. Cl.
*G01N 33/68* (2006.01)
*C07K 16/18* (2006.01)

(52) U.S. Cl.
CPC ...................................... *C07K 16/18* (2013.01)

(58) Field of Classification Search
None
See application file for complete search history.

(56) References Cited

PUBLICATIONS

Byron et al.( PloS one 7.10 (2012): e46823: 12 pages).*
Zhang et al. (Biochemical and Biophysical Research Communications 395 (2010) 275-280).*
ING-4 (A-8) datasheet, Santa Cruz Biotechnology(2010).*

* cited by examiner

*Primary Examiner* — Juliet Switzer
*Assistant Examiner* — Sahana Kaup

(57) ABSTRACT

The present invention is directed to a monoclonal antibody that recognizes human ING4 in its native form. The invention is also directed to a hybridoma cell line that produces the monoclonal antibody, and to methods of diagnosing cancer using the antibody.

7 Claims, 7 Drawing Sheets
(3 of 7 Drawing Sheet(s) Filed in Color)

ly in breast cancer cells. Byron et al. (2012)
HYBRIDOMA CLONES AND MONOCLONAL ANTIBODIES TO ING4

CROSS-REFERENCE TO RELATED APPLICATIONS

The present application claims priority to U.S. Application No. 61/718,177, filed Oct. 24, 2012, the entire contents and disclosure of which are herein incorporated by reference.

STATEMENT REGARDING FEDERALLY SPONSORED RESEARCH

This invention was made with government support under NCI 5K01CA115681 awarded by the National Institutes of Health. The government has certain rights in the invention.

INCORPORATION-BY-REFERENCE OF MATERIAL ELECTRONICALLY FILED

Incorporated by reference in its entirety herein is a computer-readable nucleotide/amino acid sequence listing submitted concurrently herewith and identified as follows: One 10 kilobyte ASCII (text) file named "ING4Seq_List_ST25" created on Oct. 22, 2013.

FIELD OF THE INVENTION

This application relates to hybridoma clones and monoclonal antibodies, and more particularly, hybridoma clones and monoclonal antibodies directed to Inhibitor of Growth 4 (ING4) protein and methods of use.

BACKGROUND OF THE INVENTION

ING4 is a member of the ING tumor suppressor family and has been shown to play a role in many cancer-related cellular processes, including, cell proliferation, apoptosis, migration, angiogenesis, contact inhibition, DNA damage response, and hypoxia. Gene deletion or reduced expression of ING4 has been reported in various cancers including glioma, breast cancer, head and neck carcinoma, melanoma, hepatocellular carcinoma, gastric carcinoma, colon cancer, and lung cancer, implicating a tumor suppressive role of ING4 in diverse tissue types. ING4 null mice, however, do not show increased spontaneous tumor formation, suggesting that ING4 deficiency alone may not be sufficient to initiate tumorigenesis (Coles et al. (2010) Proc Natl Acad Sci USA 107:11423). ING4 was identified in a genetic screen for candidate tumor suppressors that could suppress loss of contact inhibition in tissue culture (Kim et al. (2004) Proc Natl Acad Sci USA 101:16251). Subsequently, it was shown that ING4 suppressed T47D breast cancer cell growth in soft agar and MYC-initiated mammary hyperplasia in a mouse model, providing evidence for the ING4 tumor suppressor function in breast cancer (Kim et al. (2010) Cancer Res 70:5155). Recently, it was reported that 16.5% of breast tumors harbored an ING4 gene deletion, suggesting a tumor suppressive role of ING4 in at least a subset of breast cancer (Tapia et al. (2011) Hum Pathol 42:983).

Functionally, ING4 is characterized as a transcription regulator with a mechanism involving chromatin remodeling. ING4 contains a plant homeodomain (PHD) finger motif conserved among the ING family members and other transcription factors. ING4 binds to tri-methylated histone H3 at lysine 4 (H3K4me3) via the PHD. In addition, ING4 co-purifies with the HBO1/JADE histone acetyltransferase (HAT) complex, supporting a role of ING4 in chromatin modification. As H3K4me3 and HAT are generally associated with active transcription, ING4 is known to activate gene transcription in response to DNA damage. In glioma and melanoma cancer models, ING4 repressed several NF-κB-target genes, thereby attenuating tumor angiogenesis and growth (Garkavtsev et al. (2004) Nature 428:328; Li et al. (2010) Cancer Res 70:10445; Nozell et al. (2008) Mol Cell Biol 28:6632). Additionally, ING4 has been shown to represses NF-κB in breast cancer cells. Byron et al. (2012) PLOS ONE 7(10):e46823

A need exists for anti-ING4 antibodies having unique genetic and amino acid structures, including unique binding and functional characteristics. The development of new anti-ING4 monoclonal antibodies and hybridoma cells lines that produce such monoclonal antibodies would be a valuable tool for the effective diagnosis of various cancers.

SUMMARY

Some embodiments of the invention include antibodies and fragments thereof that bind to ING4. The invention is also directed to one or more hybridoma cell lines that produces the one or more antibodies that specifically bind to ING4, and to methods of diagnosing cancer using the antibody or antigen-binding fragments thereof. In some embodiments, the antibodies are monoclonal antibodies.

Some embodiments of the invention include antibodies and fragments thereof that bind to native ING4 polypeptide. For example, at least some of the antibodies specifically bind to an ING4 polypeptide of SEQ ID NO:1. In other aspects, at least some of the antibodies binds to ING4 polypeptides or fragments thereof that comprise SEQ ID NO:2, SEQ ID NO:8, and/or SEQ ID NO:9.

The antibodies of the present invention are preferably isolated monoclonal antibodies having specific binding properties against a human ING4 protein, more preferably against human ING4 in its native form. The antibodies may be labeled with one or more labels selected from the group consisting of a biotin label, a fluorescent label, an enzyme label, a coenzyme label, a chemiluminescent label, and a radioactive isotope label. In some aspects, the antibodies of the present invention may be capable of specifically binding to ING4 and or an antigenic portion thereof in normal and neoplastic cells.

Some embodiments of the invention may be used to diagnose or treat a cancer selected from glioma, breast cancer, head and neck carcinoma, melanoma, hepatocellular carcinoma, gastric carcinoma, colon cancer, prostate cancer, and lung cancer.

Some embodiments of the present invention are also directed to a method for diagnosing cancer, wherein the method comprises: reacting an anti-ING4 antibody with a sample collected from the subject, wherein the sample is at least one sample selected from the group consisting of a tissue sample, a blood sample, a serum sample, a plasma sample, and any bodily fluids, including saliva, cerebrospinal fluid, semen, interstitial fluid, and amniotic fluid; detecting an ING4 protein in the sample, and diagnosing cancer when the level of ING4 protein is lower in the sample than in a normal sample. In one embodiment, the method of diagnosing cancer further comprises reacting an anti-p-p65/RelA antibody with the sample; detecting a p-p65/RelA protein; and diagnosing cancer when the level of p-p65/RelA protein is higher in the sample than in a normal sample.

Some embodiments of the invention include a monoclonal antibody that is produced by one or more hybridoma cell lines. For example, the invention includes a monoclonal antibody comprising the same epitope specificity as a monoclonal antibody produced by hybridoma cell line BTIM-4, which has been deposited with the ATCC. Other embodiments include monoclonal antibodies selected from the group consisting of a monoclonal antibody produced by hybridoma cell line BTIM-2, BTIM-3, or BTIM-4, all of which have been deposited at the ATCC.

Some embodiments of the invention further include a method of producing an isolated antibody or fragment thereof such that the method comprises initially immunizing an animal with a polypeptide comprising an amino acid sequence of SEQ ID NO:2. The method further includes harvesting the spleen cells form the animal and fusing the spleen cells with a myeloma cell line. The method also comprises culturing the fused cells under conditions that allow production of the antibody.

Additional objectives, advantages and novel features will be set forth in the description which follows or will become apparent to those skilled in the art upon examination of the drawings and detailed description which follows.

REFERENCE TO COLOR FIGURES

This application contains at least one photograph executed in color. Copies of this patent application publication with color photographs will be provided by the Office upon request and payment of the necessary fee.

BRIEF DESCRIPTION OF THE DRAWINGS

Illustrative and exemplary embodiments of the invention are shown in the drawings in which.

DETAILED DESCRIPTION OF THE INVENTION

Figure 1:
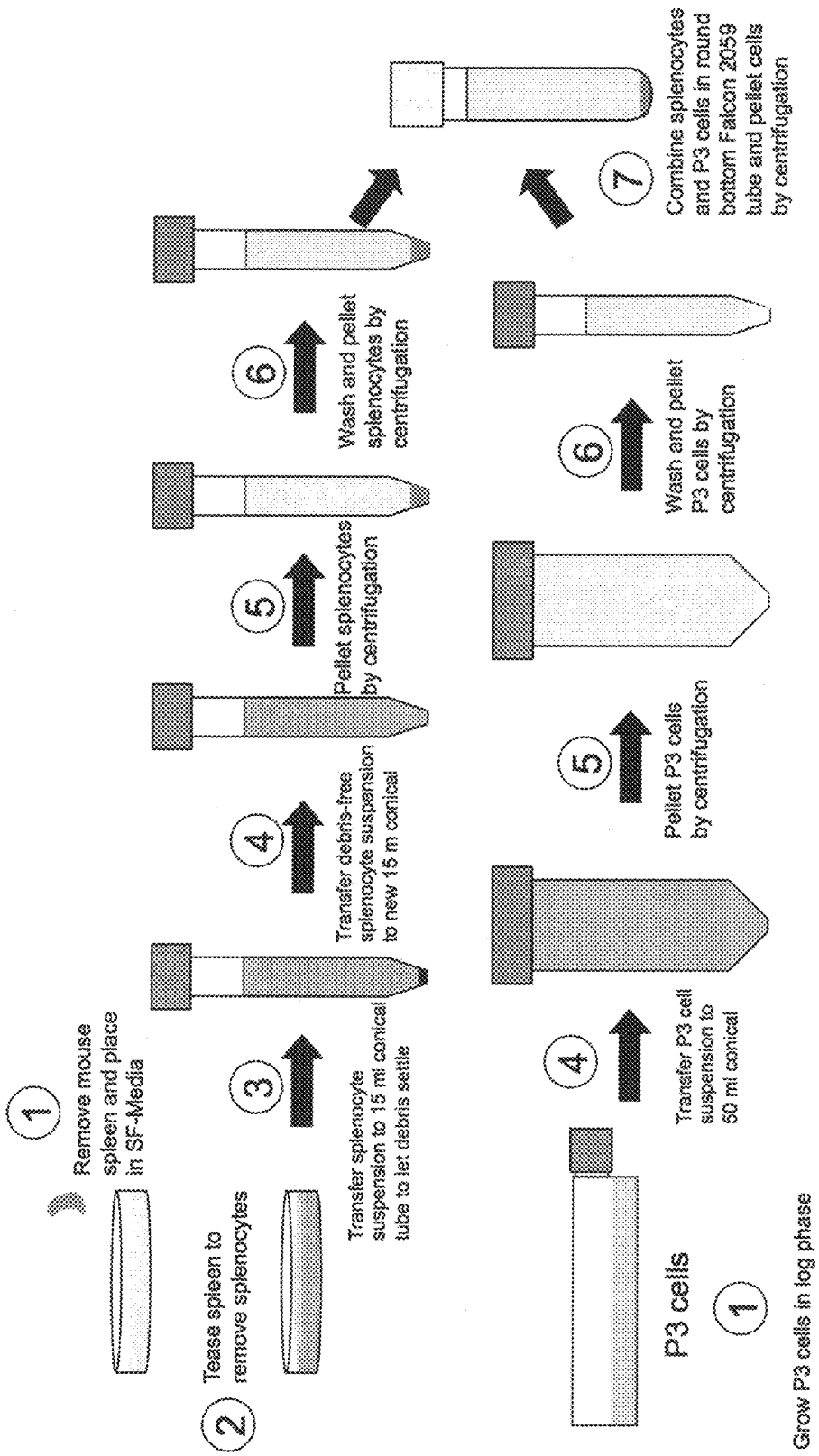
FIG. 1 illustrates the steps taken to produce hybridomas disclosed herein.

The present invention is directed to an antibody that recognizes human ING4. The invention is also directed to a hybridoma cell line that produces the antibody, and to methods of diagnosing and treating cancer using the antibody. More specifically, the inventors produced six murine hybridoma clones that secrete murine monoclonal antibodies to the human ING4 protein that are designated BTIM-1, BTIM-2, BTIM-3, BTIM-4, BTIM-5, and BTIM-6. The anti-ING4 monoclonal antibodies recognize human ING4 in its native form. See Byron et al. (2012) PLOS ONE 7(10):e46823, which is hereby incorporated by reference in its entirety.

The term "antibody" is used herein in the broadest sense and refers generally to a molecule that contains at least one antigen binding site that immunospecifically binds to a particular antigen target of interest. The term "antibody" thus includes but is not limited to native antibodies and variants thereof, fragments of native antibodies and variants thereof, peptibodies and variants thereof, and antibody mimetics that mimic the structure and/or function of an antibody or a specified fragment or portion thereof, including single chain antibodies and fragments thereof. The term "antibody," thus, includes full length antibodies and/or their variants, as well as fragments thereof. Binding of an antibody to a target can cause a variety of effects, such as but not limited to where such binding modulates, decreases, increases, antagonizes, agonizes, mitigates, alleviates, blocks, inhibits, abrogates and/or interferes with at least one target activity or binding, or with receptor activity or binding, in vitro, in situ, and/or in vivo. The present invention, thus, encompasses antibody fragments capable of binding to a biological molecule (such as an antigen or receptor) or portions thereof, including but not limited to Fab, Fab' and F(ab')$_2$, facb, pFc', Fd, Fv or scFv fragments. (See, e.g., CURRENT PROTOCOLS IN IMMUNOLOGY, (Colligan et al. eds., John Wiley & Sons, Inc., NY, 1994-2001)); diabodies; linear antibodies (Zapata et al. (1995) Protein Eng. 8(10):1057); single-chain antibody molecules; and multispecific antibodies formed from antibody fragments.

Accordingly, antibody is used in the broadest sense and specifically covers, for example, single anti-ING4 monoclonal antibodies (including agonist, antagonist, and neutralizing antibodies), anti-ING4 antibody compositions with polyepitopic specificity, single chain anti-ING4 antibodies, and fragments of anti-ING4 antibodies. The term "monoclonal antibody" as used herein refers to an antibody obtained from a population of substantially homogeneous antibodies, i.e., the individual antibodies comprising the population are identical except for possible naturally-occurring mutations that may be present in minor amounts.

"Fv" is the minimum antibody fragment that contains a complete antigen-recognition and antigen-binding site. This region consists of a dimer of one heavy- and one light-chain variable domain in tight, non-covalent association. It is in this configuration that the three CDRs of each variable domain interact to define an antigen-binding site on the surface of the $V_H$-$V_L$ dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

The Fab fragment also contains the constant domain of the light chain and the first constant domain (CH1) of the heavy chain. Fab fragments differ from Fab' fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

The "light chains" of antibodies (immunoglobulins) from any vertebrate species can be assigned to one of two clearly distinct types, called kappa and lambda, based on the amino acid sequences of their constant domains.

Depending on the amino acid sequence of the constant domain of their heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA, and IgA2.

"Single-chain Fv" or "sFv" antibody fragments comprise the VH and VL domains of antibody, wherein these domains are present in a single polypeptide chain. Preferably, the Fv polypeptide further comprises a polypeptide linker between the $V_H$ and $V_L$ domains, which enables the sFv to form the desired structure for antigen binding. For a review of sFv, see Pluckthun in The Pharmacology of Monoclonal Antibodies, vol. 113, Rosenburg and Moore eds., Springer-Verlag, New York, pp. 269-315 (1994).

The term "diabodies" refers to small antibody fragments with two antigen-binding sites, which fragments comprise a heavy-chain variable domain ($V_H$) connected to a light-chain variable domain ($V_L$) in the same polypeptide chain ($V_H$-$V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al. (1993) Proc. Natl. Acad. Sci. USA 90:6444.

An "isolated" antibody is one that has been identified and separated and/or recovered from a component of its natural environment. Contaminant components of its natural environment are materials, which would interfere with diagnostic or therapeutic uses for the antibody, and may include enzymes, hormones, and other proteinaceous or nonproteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

A "native sequence ING4 polypeptide" comprises a polypeptide having the same amino acid sequence as the corresponding ING4 polypeptide derived from nature. Such native sequence ING4 polypeptides can be isolated from nature or can be produced by recombinant or synthetic methods. The term "native sequence ING4 polypeptide" specifically encompasses naturally-occurring truncated or secreted forms of the specific ING4 polypeptide (e.g., an extracellular domain sequence), naturally-occurring variant forms (e.g., alternatively spliced forms) and naturally-occurring allelic variants of the polypeptide. In various embodiments of the invention, the native sequence ING4 polypeptides disclosed herein are mature or full-length native sequence polypeptides comprising the full-length amino acid sequences recited herein. In some embodiments, the "native sequence ING4 polypeptide" comprises an amino acid sequence of SEQ ID NO:1 or a fragment thereof, as described in greater detail herein.

The terms "individual," "subject," and "patient," used interchangeably herein, refer to an animal, preferably a mammalian (including a nonprimate and a primate), including, but not limited to, murines, simians, humans, mammalian farm animals (e.g., bovine, porcine, ovine), mammalian sport animals (e.g., equine), and mammalian pets (e.g., canine and feline); preferably the term refers to humans.

As used herein, the terms "treatment", "treating", and the like, refer to obtaining a desired pharmacologic, and/or physiologic effect. The effect may be therapeutic in terms of a partial or complete cure for a disease and/or adverse effect attributable to the disease. "Treatment," as used herein, includes administration of a compound of the present invention for treatment of a disease or condition in a mammal, particularly in a human, and includes: (a) inhibiting the disease, i.e., arresting its development; (b) providing palliative care, i.e., reducing and preventing the suffering of a patient; and (c) relieving the disease, i.e., causing regression of the disease or disorder or alleviating symptoms or complications thereof. Dosage regimens may be adjusted to provide the optimum desired response.

As used herein, the term "epitope" refers to a portion of an antigenic molecule to which an antibody is produced and to which the antibody will bind. An "ING4 epitope" comprises the part of the ING4 protein to which an ING4 monoclonal antibody specifically binds. Epitopes can comprise linear amino acid residues (i.e., residues within the epitope are arranged sequentially one after another in a linear fashion), nonlinear amino acid residues, or both linear and nonlinear amino acid residues. Typically epitopes are generally short amino acid sequences (e.g. about five amino acids in length).

Monoclonal Antibodies

The anti-ING4 antibodies may, alternatively, be monoclonal antibodies. Monoclonal antibodies may be prepared using hybridoma methods, such as those described by Kohler and Milstein (1975) Nature 256:495. In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes may be immunized in vitro.

An immunizing agent typically includes the ING4 polypeptide, a portion thereof, or a fusion protein thereof. Generally, either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell (Goding (1986) Monoclonal Antibodies: Principles and Practice, Academic Press, pp. 59-103). Immortalized cell lines may be transformed mammalian cells, particularly myeloma cells of rodent, bovine, and human origin. Rat or mouse myeloma cell lines may be employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Manassas, Va. Human myeloma and mouse-human heteromyeloma cell lines also have been described for the production of human monoclonal antibodies (Kozbor (1984) J. Immunol. 133:3001; Brodeuretal (1987) Monoclonal Antibody Production Techniques and Applications, Marcel Dekker, Inc., New York, pp. 51-631).

The culture medium in which the hybridoma cells are cultured can then be assayed for the presence of monoclonal antibodies directed against ING4. The binding specificity of monoclonal antibodies produced by the hybridoma cells can be determined by inmunoprecipitation or by an in vitro binding assay, such as radioimmunoassay (RIA) or enzyme-linked immunosorbent assay (ELISA). Such techniques and assays are known in the art. The binding affinity of the monoclonal antibody can, for example, be determined by the Scatchard analysis of Munson and Pollard (1980) Anal. Biochem. 107:220.

After the desired hybridoma cells are identified, the clones may be subcloned by limiting dilution procedures and grown by standard methods (coding, supra). Suitable culture media for this purpose include, for example, Dulbecco's Modified Eagle's Medium and RPMI-1640 medium. Alternatively, the hybridoma cells may be grown in vivo as ascites in a mammal.

The monoclonal antibodies secreted by the subclones may be isolated or purified from the culture medium or ascites fluid by conventional immunoglobulin purification procedures, such as, protein A-Sepharose, hydroxylapatite chromatography, gel electrophoresis, dialysis, or affinity chromatography.

The monoclonal antibodies may also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA may be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences (U.S. Pat. No. 4,816,567; Morrison et al., supra) or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

The antibodies may be monovalent antibodies. Methods for preparing monovalent antibodies are well known in the art. For example, one method involves recombinant expression of immunoglobulin light chain and modified heavy chain. The heavy chain is truncated generally at any point in the Fc region so as to prevent heavy chain crosslinking. Alternatively, the relevant cysteine residues are substituted with another amino acid residue or are deleted so as to prevent crosslinking.

In vitro methods are also suitable for preparing monovalent antibodies. Digestion of antibodies to produce fragments thereof can be accomplished using routine techniques known in the art.

The anti-ING4 monoclonal antibodies of the invention may be whole or an antigen-binding fragment of the antibody that specifically binds an ING4 polypeptide, preferably a native sequence ING4 polypeptide (e.g., an ING4 polypeptide of SEQ ID NO:1 or a fragment thereof). Furthermore, in a preferred embodiment the monoclonal antibody is identified as lab number mAb BTIM-1, BTIM-2, BTIM-3, BTIM-4, BTIM-5, or BTIM-6 having recognition of an ING4 protein from at least one cancer cell line.

In one non-limiting embodiment the monoclonal antibody is produced by a hybridoma cell line, such that the antibody or functional fragment thereof binds to an ING4 protein or a fragment thereof. In one embodiment, the monoclonal antibody is of a murine IgG1, kappa chain isotype.

More specifically, the monoclonal antibody of the invention comprises a heavy chain variable region (HCVR) and a light chain variable region (LCVR), wherein said HCVR comprises: a) a peptide at CDRH1, b) a peptide at CDRH2, c) a peptide at CDRH3, and wherein said LCVR comprises: a) a peptide at CDRL1, b) a peptide at CDRL2, and c) a peptide at CDRL3.

Human and Humanized Antibodies

The murine monoclonal antibodies of the present invention can be humanized to reduce the immunogenicity for use in humans. Humanized forms of non-human (e.g., murine) antibodies are chimeric immunoglobulins, immunoglobulin chains or fragments thereof (such as, Fv, Fab, Fab', F(ab')$_2$, or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues, which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin (Jones et al, (1986) Nature 321:522; Riechmann et al. (1988) Nature 332:323; and, Presta (1992) Curr. Op. Struct. Biol. 2:593).

Methods for humanizing non-human antibodies are well known in the art. An example approach is to make mouse-human chimeric antibodies having the original variable region of the murine monoclonal antibodies, joined to constant regions of a human immunoglobulin. Chimeric antibodies and methods for their production are known in the art. See, e.g., Cabilly et al. European Patent EP0125023 (published Nov. 14, 1984); Taniguchi et al., European Patent EP0171496 (published Feb. 19, 1986); Morrison et al., European Patent Application EP0173494 (published Jan. 18, 1986); Neuberger et al., International Publication No. WO/1986/01533, (published Mar. 13, 1986); Kudo et al., European Patent Application EP0184187 (published Jun. 11, 1986); Robinson et al., International Publication No. WO/1987/002671 (published May 7, 1987); Liu et al. (1987) Proc. Natl. Acad. Sci. USA 84: 3439-3443; Sun et al. (1987) Proc. Natl. Acad. Sci. USA 84: 214-218; Better et al. (1988) Science 240: 1041-1043. These references are incorporated herein by reference. Generally, DNA segments encoding the H and L chain antigen-binding regions of the murine mAb can be cloned from the mAb-producing hybridoma cells, which can then be joined to DNA segments encoding $C_H$ and $C_L$ regions of a human immunoglobulin, respectively, to produce murine-human chimeric immunoglobulin-encoding genes.

Generally, a humanized antibody has one or more amino acid residues introduced into it from a source that is non-human. These non-human amino acid residues are often referred to as "import" residues, which are typically taken from an "import" variable domain. Humanization can be essentially performed following the method of Winter and co-workers (Jones et al. (1986) Nature, 321:522-525; Riechmann et al. (1988) Nature, 332:323-327; Verhoeyen et al. (1988) Science, 239:1534-1536), by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Pharmaceutical Compositions of Antibodies

In other embodiments there is provided a pharmaceutical composition including an antibody or fragment as described above together with a pharmaceutically acceptable carrier, diluent or excipient.

In the preparation of the pharmaceutical compositions comprising the antibodies described in the teachings herein, a variety of vehicles and excipients and routes of administration may be used, as will be apparent to the skilled artisan. Representative formulation technology is taught in, inter alia, Remington: The Science and Practice of Pharmacy, 19th Ed., Mack Publishing Co., Easton, Pa. (1995) and Handbook of Pharmaceutical Excipients, 3rd Ed, Kibbe, A. H. ed., Washington D.C., American Pharmaceutical Association (2000); hereby incorporated by reference in their entirety.

The pharmaceutical compositions will generally comprise a pharmaceutically acceptable carrier and a pharmacologically effective amount of the antibodies, or mixture of antibodies.

The pharmaceutical composition may be formulated as powders, granules, solutions, suspensions, aerosols, solids, pills, tablets, capsules, gels, topical creams, suppositories, transdermal patches, and other formulations known in the art.

For the purposes described herein, pharmaceutically acceptable salts of the antibodies is intended to include any art recognized pharmaceutically acceptable salts including organic and inorganic acids and/or bases. Examples of salts include sodium, potassium, lithium, ammonium, calcium, as well as primary, secondary, and tertiary amines, esters of lower hydrocarbons, such as methyl, ethyl, and propyl. Other salts include organic acids, such as acetic acid, propionic acid, pyruvic acid, maleic acid, succinic acid, tartaric acid, citric acid, benzoic acid, cinnamic acid, salicylic acid, etc.

As used herein, "pharmaceutically acceptable carrier" comprises any standard pharmaceutically accepted carriers known to those of ordinary skill in the art in formulating pharmaceutical compositions. Thus, the antibodies or peptides, by themselves, such as being present as pharmaceutically acceptable salts, or as conjugates, may be prepared as formulations in pharmaceutically acceptable diluents; for example, saline, phosphate buffer saline (PBS), aqueous ethanol, or solutions of glucose, mannitol, dextran, propylene glycol, oils (e.g., vegetable oils, animal oils, synthetic oils, etc.), microcrystalline cellulose, carboxymethyl cellulose, hydroxylpropyl methyl cellulose, magnesium stearate, calcium phosphate, gelatin, polysorbate 80 or as solid formulations in appropriate excipients.

The pharmaceutical compositions will often further comprise one or more buffers (e.g., neutral buffered saline or phosphate buffered saline), carbohydrates (e.g., glucose, sucrose or dextrans), mannitol, proteins, polypeptides or amino acids such as glycine, antioxidants (e.g., ascorbic acid, sodium metabisulfite, butylated hydroxytoluene, butylated hydroxyanisole, etc.), bacteriostats, chelating agents such as EDTA or glutathione, adjuvants (e.g., aluminium hydroxide), solutes that render the formulation isotonic, hypotonic or weakly hypertonic with the blood of a recipient, suspending agents, thickening agents and/or preservatives. Alternatively, compositions of the present invention may be formulated as a lyophilizate.

While any suitable carrier known to those of ordinary skill in the art may be employed in the compositions of this invention, the type of carrier will typically vary depending on the mode of administration. Antibody compositions may be formulated for any appropriate manner of administration, including for example, oral, nasal, mucosal, intravenous, intraperitoneal, intradermal, subcutaneous, and intramuscular administration.

For parenteral administration, the compositions can be administered as injectable dosages of a solution or suspension of the substance in a physiologically acceptable diluent with a pharmaceutical carrier that can be a sterile liquid such as sterile pyrogen-free water, oils, saline, glycerol, polyethylene glycol, or ethanol. Additionally, auxiliary substances, such as wetting or emulsifying agents, surfactants, pH buffering substances and the like can be present in compositions.

Other components of pharmaceutical compositions are those of petroleum, animal, vegetable, or synthetic origin, for example, non-aqueous solutions of peanut oil, soybean oil, corn oil, cottonseed oil, ethyl oleate, and isopropyl myristate. Antibodies can be administered in the form of a depot injection or implant preparation, which can be formulated in such a manner as to permit a sustained release of the active ingredient. An exemplary composition comprises antibody at 5 mg/ml, formulated in aqueous buffer consisting of 50 mM L-histidine, 150 mM NaCl, adjusted to pH 6.0 with HCl.

Typically, the compositions are prepared as injectables, either as liquid solutions or suspensions; solid or powder forms suitable for reconstitution with suitable vehicles, including by way example and not limitation, sterile pyrogen free water, saline, buffered solutions, dextrose solution, etc., prior to injection. The preparation also can be emulsified or encapsulated in liposomes or micro particles such as polylactide, polyglycolide, or copolymers.

The pharmaceutical compositions described herein may be presented in unit-dose or multi-dose containers, such as sealed ampoules or vials. Such containers are typically sealed in such a way to preserve the sterility and stability of the formulation until use. In general, formulations may be stored as suspensions, solutions or emulsions in oily or aqueous vehicles, as indicated above.

Alternatively, a pharmaceutical composition may be stored in a freeze-dried condition requiring only the addition of a sterile liquid carrier immediately prior to use.

Uses for Anti-ING4 Antibodies

The anti-ING4 antibodies of the invention have various utilities. In one embodiment, anti-ING4 antibodies may be used in diagnostic or prognostic assays for ING4, e.g., detecting its expression in specific cells, tissues, or serum. Various diagnostic and prognostic assay techniques known in the art may be used, such as competitive binding assays, direct or indirect sandwich assays and immunoprecipitation assays conducted in either heterogeneous or homogeneous phases (Zola, Monoclonal Antibodies: A Manual of Techniques, CRC Press, Inc. (1987) pp. 147-1581). The antibodies used in the assays can be labeled with a detectable moiety. The detectable moiety should be capable of producing, either directly or indirectly, a detectable signal. Any method known in the art for conjugating the antibody to the detectable moiety may be employed, including those methods described by Hunter et al. (1962) Nature, 144:945; David et al. (1974) Biochemistry, 13:1014; Pain et al. (1981) J. Immunol. Meth., 40:219; and Nygren, J. Histochem. and Cytochem., 30:407 (1982).

"Detecting" refers to determining the presence, absence, or amount of an analyte in a sample, and can include quantifying the amount of the analyte in a sample or per cell in a sample.

"Diagnostic" refers to identifying the presence or nature of a pathologic condition. Diagnostic methods differ in their specificity and sensitivity. While a particular diagnostic method may not provide a definitive diagnosis of a condition, it suffices if the method provides a positive indication that aids in diagnosis.

"Immunoassay" refers to a method of detecting an analyte in a sample involving contacting the sample with an antibody that specifically binds to the analyte and detecting binding between the antibody and the analyte.

"Immunohistochemical" (abbreviated IHC) refers to specific binding agents, such as polyclonal and monoclonal antibodies, which recognize and mark antigens of interest, often by a chemical that shows that the agent has bound to the antigen of interest. An example of an IHC agent is an ING4 monoclonal antibody.

The present invention relates to diagnostic assays, both quantitative and qualitative for detecting levels of ING4 polypeptide in cells, tissues and bodily fluids, including determination of normal and abnormal levels. Assay techniques that can be used to determine levels of a polypeptide, such as ING4, in a sample derived from a host are well-known to those of skill in the art. Such assay methods include, but are not limited to, radioimmunoassays, immunohistochemistry assays, in situ hybridization assays, competitive-binding assays, Western Blot analyses and ELISA assays. Among these, ELISAs are frequently used to detect a gene's expressed protein in biological fluids. An ELISA assay initially comprises preparing an antibody specific to ING4, preferably a monoclonal antibody. In addition, a reporter antibody generally is prepared which binds specifically to ING4. The reporter antibody is attached to a detectable reagent such as a radioactive, fluorescent or enzymatic reagent, for example horseradish peroxidase enzyme or alkaline phosphatase.

The above tests can be carried out on samples derived from patients' bodily fluids (e.g., saliva, cerebrospinal fluid, semen, interstitial fluid, amniotic fluid, etc.) and tissue extracts (homogenates or solubilized tissue) such as from tissue biopsy and autopsy material. Levels of ING4, determined in cells and tissues from a patient suspected of suffering from cancer by measuring the polypeptide or by transcription levels, are compared to levels of ING4 in normal or control cells or tissues. Decreased levels of ING4 measured in the patient as compared to levels in the same cells, tissues, or bodily fluids obtained from normal, healthy individuals (i.e., control samples) are indicative of cancer. By "decreased levels" it is meant a decrease in measured ING4 levels in a patient as compared to ING4 levels in the same normal cells or tissues. In some embodiments, "decreased levels" may include undetectable ING4 levels in a patient as compared to ING4 levels in the same or normal tissues. Detection of decreased ING4 levels is useful in the diagnosis of various cancers including, but not limited to, glioma, breast cancer, head and neck carcinoma, melanoma, hepatocellular carcinoma, gastric carcinoma, colon cancer, prostate cancer, and lung cancer.

Further, monitoring of ING4 levels in a patient diagnosed with cancer is useful in determining the onset of metastases in cancers that have not yet metastasized and in determining the stage of the cancer. For example, detection of ING4 can be used in a method of monitoring cancer in a patient that has not metastasized for the onset of metastasis. In this method, a patient suffering from a cancer (e.g., breast cancer) that is not known to have metastasized is identified. ING4 levels in a sample from the patient are then measured. These measured ING4 levels are then compared with levels of ING4 from a normal control sample. A decrease in measured ING4 levels in the patient versus the normal control is associated with a cancer that has metastasized.

The stage of cancer in a patient suffering from, for example, breast cancer can also be determined. In this method a patient suffering from cancer is identified. ING4 levels in a sample of tissue from the patient are measured to establish a baseline ING4 level for said patient. ING4 levels in samples of the same tissue are then determined at subsequent time periods such as scheduled check-ups with the patient's physician. Measured ING4 levels are then compared with the baseline ING4 levels for the patient. In this method, a decrease in measured ING4 levels in the patient versus baseline ING4 levels in the patient is associated with a cancer that is progressing and an increase in measured ING4 levels versus baseline ING4 levels is associated with a cancer that is regressing or in remission. Decreases in measured ING4 levels as compared to baseline ING4 levels established for the patient may also be indicative of metastases.

In one embodiment, ING4 immunohistochemistry functions as an "index diagnostic" to assign risk based on the presence of ING4 expression. Therefore, based on this and other parameters (e.g., size of lesion), one can determine whether or not different therapeutic modalities (i.e., chemotherapy, radiation therapy, surgery) should be used. In a related aspect, methods for monitoring progression of premalignancy into a malignant phenotype are disclosed. For example, by using serial sampling (i.e., biopsy) of the tissue and observing the state of ING4 protein levels in the lesions, one can determine whether or not the premalignancies are progressing in a way that would indicate whether therapeutic intervention is advised or is successful.

One aspect of the invention is a method to determine the likelihood of a group of cells to become cancerous e.g., for these cells or glands to become premalignancies or progress to cancerous lesions. The invention utilizes an agent, such as an antibody, that specifically binds to ING4 protein to assess levels of ING4 in tissue and cells. ING4 expression in cells and tissue may also be assessed using nucleic acid analysis, such as selective amplification, or hybridization methods. A level of ING4 below normal or control levels, indicates an increased likelihood that premalignant disease is present i.e., that the cells or tissues are premalignant.

In another embodiment, the anti-ING4 antibodies are useful for a method of treatment of a disease, such as cancer. The method of the invention preferably includes the step of providing an antibody or ING4 antigen-binding fragment thereof, as described above, to a subject requiring said treatment.

Methods of immunotargeting cancer cells using antibodies or antibody fragments are well known in the art. U.S. Pat. No. 6,306,393, for instance, describes the use of anti-CD22 antibodies in the immunotherapy of B-cell malignancies, and U.S. Pat. No. 6,329,503 describes immunotargeting of cells that express serpentine transmembrane antigens. Antibodies described herein (including humanized or human monoclonal antibodies or fragments or other modifications thereof, optionally conjugated to cytotoxic or other agents) can be introduced into a patient such that the antibody binds to cancer cells and mediates the destruction of the cells and the tumor and/or inhibits the growth of the cells or the tumor.

Without intending to limit the disclosure, mechanisms by which such antibodies can exert a therapeutic effect may include complement-mediated cytolysis, antibody-dependent cellular cytotoxicity (ADCC) modulating the physiologic function of the tumor antigen, inhibiting binding or signal transduction pathways, modulating tumor cell differentiation, altering tumor angiogenesis factor profiles, modulating the secretion of immune stimulating or tumor suppressing cytokines and growth factors, modulating cellular adhesion, and/or by inducing apoptosis.

The antibodies can also be conjugated to toxic or therapeutic agents, such as radioligands, dyes, fluorescent and/or luminescent agents, or cytosolic toxins, and may also be used therapeutically to deliver the toxic or therapeutic agent directly to tumor cells. Moreover, in some embodiments of the invention, the labeled antibodies may be used to label cells in vivo or in vitro to determine levels of expression of ING4 protein. As such, the labeled cells may be directly or indirectly imaged via secondary methods that are applicable to each labeling agent.

By "treatment" herein is meant therapeutic, prophylactic, palliative, or suppressive treatment for the disease, disorder or undesirable condition. Treatment encompasses administration of the subject antibodies in an appropriate form prior to the onset of disease symptoms and/or after clinical manifestations, or other manifestations, of the disease to reduce disease severity, halt disease progression, or eliminate the disease. Prevention of the disease includes prolonging or delaying the onset of symptoms of the disorder or disease, preferably in a subject with increased susceptibility to the disease.

The therapeutic preparations can use non-modified antibodies or antibodies conjugated with a therapeutic compound, such as a toxin or cytotoxic molecule, depending on the functionality of the antibody. Generally, when non-modified antibodies are used, they will typically have a functional Fc region. By "functional Fc region" herein is meant a minimal sequence for affecting the biological function of Fc, such as binding to Fc receptors, particularly FcγR (e.g., Fcγ RI, FcγRII, and FcγRIII).

Without being bound by theory, it is believed that the Fc region may affect the effectiveness of anti-tumor monoclonal antibodies by binding to Fc receptors immune effector cells and modulating cell mediated cytotoxicity, endocytosis, phagocytosis, release of inflammatory cytokines, complement mediate cytotoxicity, and antigen presentation. In this regard, polyclonal antibodies, or mixtures of monoclonal antibodies will be advantageous because they will bind to different epitopes and thus have a higher density of Fc on the cell surface as compared to when a single monoclonal antibody is used. Of course, to enhance their effectiveness in depleting targeted cells, or where non-modified antibodies are not therapeutically effective, antibodies conjugated to toxins or cytotoxic agents may be used.

The antibody compositions may be used either alone or in combination with other therapeutic agents to increase efficacy of traditional treatments or to target abnormal cells not targeted by the antibodies. The antibodies and antibody compositions of the invention include PEGylated antibodies and/or pretargeting constructs of the antibodies. Combining the antibody therapy method with a chemotherapeutic, radiation or surgical regimen may be preferred in patients that have not received chemotherapeutic treatment, whereas treatment with the antibody therapy may be indicated for patients who have received one or more chemotherapies. Additionally, antibody therapy can also enable the use of reduced dosages of concomitant chemotherapy, particularly in patients that do not tolerate the toxicity of the chemotherapeutic agent very well. Furthermore, treatment of cancer patients with the antibody with tumors resistant to chemotherapeutic agents might induce sensitivity and responsiveness to these agents in combination.

In one aspect, the antibodies are used adjunctively with therapeutic cytotoxic agents, including, by way of example and not limitation, busulfan, thioguanine, idarubicin, cytosine arabinoside, 6-mercaptopurine, doxorubicin, daunorubicin, etoposide, and hydroxyurea. Other agents useful as adjuncts to antibody therapy are compounds directed specifically to the abnormal cellular molecule found in the disease state. These agents will be disease specific.

The amount of the compositions needed for achieving a therapeutic effect will be determined empirically in accordance with conventional procedures for the particular purpose. Generally, for administering the compositions ex vivo or in vivo for therapeutic purposes, the compositions are given at a pharmacologically effective dose. By "pharmacologically effective amount" or "pharmacologically effective dose" is an amount sufficient to produce the desired physiological effect or amount capable of achieving the desired result, particularly for treating or retreating the disorder or disease condition, including reducing or eliminating one or more symptoms or manifestations of the disorder or disease.

As an illustration, administration of antibodies to a patient suffering from breast cancer provides a therapeutic benefit not only when the underlying disease is eradicated or ameliorated, but also when the patient reports a decrease in the severity or duration of the symptoms associated with the disease. Therapeutic benefit also includes halting or slowing the progression of the underlying disease or disorder, regardless of whether improvement is realized.

The amount administered to the subject will vary depending upon what is being administered, the purpose of the administration, such as prophylaxis or therapy, the state of the host, the manner of administration, the number of administrations, interval between administrations, and the like. These can be determined empirically by those skilled in the art and may be adjusted for the extent of the therapeutic response. Factors to consider in determining an appropriate dose include, but is not limited to, size and weight of the subject, the age and sex of the subject, the severity of the symptom, the stage of the disease, method of delivery of the agent, half-life of the agents, and efficacy of the agents. Stage of the disease to consider includes whether the disease is acute or chronic, relapsing or remitting phase, and the progressiveness of the disease. Determining the dosages and times of administration for a therapeutically effective amount is well within the skill of the ordinary person in the art.

For any compositions of the present disclosure, the therapeutically effective dose is readily determined by methods well known in the art. For example, an initial effective dose can be estimated from cell culture or other in vitro assays. For example, Sliwkowsky, M X et al. (1999) Semin. Oncol. 26.suppl. 12: 60-70 describes in vitro measurements of antibody dependent cellular cytotoxicity. A dose can then be formulated in animal models to generate a circulating concentration or tissue concentration, including that of the $IC_{50}$ as determined by the cell culture assays.

In addition, the toxicity and therapeutic efficacy are generally determined by cell culture assays and/or experimental animals, typically by determining a $LD_{50}$ (lethal dose to 50% of the test population) and $ED_{50}$ (therapeutically effectiveness in 50% of the test population). The dose ratio of toxicity and therapeutic effectiveness is the therapeutic index. Preferred are compositions, individually or in combination, exhibiting high therapeutic indices. Determination of the effective amount is well within the skill of those in the art, particularly given the detailed disclosure provided herein. Guidance is also found in standard reference works, for example Fingl and Woodbury, General Principles In: The Pharmaceutical Basis of Therapeutics pp. 1-46 (1975), and the references cited therein.

To achieve an initial tolerizing dose, consideration is given to the possibility that the antibodies may be immunogenic in humans and in non-human primates. The immune response may be biologically significant and may impair the therapeutic efficacy of the antibody even if the antibody is partly or chiefly comprised of human immunoglobulin sequences such as, for example, in the case of a chimeric or humanized antibody. Within certain embodiments, an initial high dose of antibody is administered such that a degree of immunological tolerance to the therapeutic antibody is established.

The tolerizing dose is sufficient to prevent or reduce the induction of an antibody response to repeat administration of the committed progenitor cell specific antibody.

Preferred ranges for the tolerizing dose are between 10 mg/kg body weight to 50 mg/kg body weight, inclusive. More preferred ranges for the tolerizing dose are between 20 and 40 mg/kg, inclusive. Still more preferred ranges for the tolerizing dose are between 20 and 25 mg/kg, inclusive.

Within these therapeutic regimens, the therapeutically effective dose of antibodies is preferably administered in the range of 0.1 to 10 mg/kg body weight, inclusive. More preferred second therapeutically effective doses are in the range of 0.2 to 5 mg/kg body weight, inclusive. Still more preferred therapeutically effective doses are in the range of 0.5 to 2 mg/kg, inclusive. Within alternative embodiments, the subsequent therapeutic dose or doses may be in the same or different formulation as the tolerizing dose and/or may be administered by the same or different route as the tolerizing dose.

For the purposes of this invention, the methods of administration are chosen depending on the condition being treated, the form of the subject antibodies, and the pharmaceutical composition.

Administration of the antibody compositions can be done in a variety of ways, including, but not limited to, continuously, subcutaneously, intravenously, orally, topically, transdermal, intraperitoneal, intramuscularly, and intravesically. For example, microparticle, microsphere, and microencapsulate formulations are useful for oral, intramuscular, or subcutaneous administrations. Liposomes and nanoparticles are additionally suitable for intravenous administrations. Administration of the pharmaceutical compositions may be through a single route or concurrently by several routes. For instance, intraperitoneal administration can be accompanied by intravenous injections. Preferably the therapeutic doses are administered intravenously, intraperitonealy, intramuscularly, or subcutaneously.

The compositions may be administered once or several times. In some embodiments, the compositions may be administered once per day, a few or several times per day, or even multiple times per day, depending upon, among other things, the indication being treated and the judgment of the prescribing physician.

Administration of the compositions may also be achieved through sustained release or long-term delivery methods, which are well known to those skilled in the art. By "sustained release or" "long term release" as used herein is meant that the delivery system administers a pharmaceutically therapeutic amount of subject compounds for more than a day, preferably more than a week, and most preferable at least about 30 days to 60 days, or longer. Long term release systems may comprise implantable solids or gels containing the antibodies, such as biodegradable polymers described above; pumps, including peristaltic pumps and fluorocarbon propellant pumps; osmotic and mini-osmotic pumps; and the like.

The method of the invention contemplates the administration of single monoclonal antibodies and any antibody that recognizes the particular antigens recognized by these antibodies, as well as combinations, of different monoclonal antibodies. Two or more monoclonal antibodies may provide an improved effect compared to a single antibody. Alternatively, a combination of an antibody with an antibody that binds a different antigen may provide an improved effect compared to a single antibody. Additionally, contrast agents may be administered in combination with the antibodies in order to improve differential labeling of neoplastic cells or lesions. Such monoclonal antibodies cocktails may have certain advantages inasmuch as they contain monoclonal antibodies, which exploit different effector mechanisms or combine directly cytotoxic monoclonal antibodies with monoclonal antibodies that rely on immune effector functionality. Such monoclonal antibodies in combination may exhibit synergistic therapeutic effects.

Antibody Kits

Antibody kits are provided which contain the necessary reagents to carry out the assays of the present invention. The kit may include one or more compartments, each to receive one or, more containers such as: (a) a first container comprising one of the components of the present invention described above; and (b) one or more other containers comprising one or more of the following: wash reagents, reagents capable of detecting presence of the antibody or peptide, and/or recombinant ING4 protein or fragments thereof as a control for detection or for a competitive assay.

The containers allow one to efficiently transfer reagents from one compartment to another compartment such that the samples and reagents are not cross-contaminated, and the agents or solutions of each container can be added in a quantitative fashion from one compartment to another.

The kit typically contains containers, which may be formed from a variety of materials such as glass or plastic, and can include for example, bottles, vials, syringes, and test tubes. A label typically accompanies the kit, and includes any writing or recorded material, which may be electronic or computer readable form (e.g., disk, optical disc, or tape) providing instructions or other information for used of the contents of the kit. The label indicates that the formulation is used for diagnosing or treating the disorder of choice.

One skilled in the art will readily recognize that the disclosed antibodies of the present invention can be readily incorporated into one of the established kit formats, which are well known in the art.

All patent and literature references cited in the present specification are hereby incorporated by reference in their entirety.

The following examples are offered for illustrative purposes only, and are not intended to limit the scope of the present invention in any way.

EXAMPLES

Multiple murine hybridoma clones that secrete murine monoclonal antibodies that bind to the human ING4 protein were generated. As described in greater detail herein, these antibodies recognize (e.g., specifically bind) human ING4 in its native form or fragments thereof.

Commercially available reagents referred to in the examples were used according to manufacturer's instructions unless otherwise indicated. The following examples are offered for illustrative purposes only, and are not intended to limit the scope of the present invention in any way.

Example 1

General Hybridoma Production and Screening Protocol

The following protocols are used for general hybridoma production in the laboratory, as well as for screening and subcloning hybridomas.

General Hybridoma Fusion Protocol

Fusion Preparation:

3-4 days prior to fusion

1) Two T-75 or one T-225 flask of myeloma cells, P3X653 (P3 cells), at $4 \times 10^5$ cell/ml (30 ml) in 10% HY Medium (or C-DMEM) were set up. Fresh media was added the day before fusion. In addition, during this timeframe, the animals that were used to generate desired lymphocytes for fusion received an intravenous booster injection. Moreover, any equipment that was to be used in harvesting tissue from the animals was autoclaved.

Day of the Fusion

On the day of fusion, Fusion Media was prepared as follows: DMEM (LTI) 128 ml, HAT (50×; Sigma) 4 ml, OPI (100×: Sigma) 2 ml, HEPES (1 M; Sigma) 2 ml, Glutamax I (100×; LTI) 2 ml, NCTC (Sigma) 20 ml, FBS (LTI) 40 ml, Pen/Strep (LTI) 2 ml, Nutridoma (BM) 1.6 ml. In addition, 50 ml of SF-DMEM with 0.5 ml of 1 M HEPES (DMEM/HEPES) was prepared. Thereafter, 9.5 ml of DMEM/HEPES and 0.5 ml DMSO was added to a conical tube (DMEM/HEPES/DMSO).

After preparation of the aforementioned media, the following were placed in a 37° C. water bath: 200 ml Fusion Media (FX-media), 40 ml DMEM/HEPES, 10 ml DMEM/HEPES/DMSO, and 1 ml aliquot of polyethylene glycol/DMSO mix (PEG/DMSO). In addition, eight flat bottom 96 well plates were labeled with fusion number, plate number, and date (e.g., FX03.5 Aug. 31, 2007) Further, 50×HAT was suspended in 10 mL of SF-DMEM and 100×OPI was suspend in 10 mL sterile water.

Fusion

FIG. 1 illustrates the steps that can be employed in the fusion process. Initially, mice that have been previously immunized with an antigen (as described in greater detail below) were sacrificed and spleens were removed. Each spleen was placed in 10 ml DMEM/HEPES in a 100 mm cell culture dish. In addition, P3 cells were harvested and counted such that between 5 and $20 \times 10^7$ cells were used for fusion.

Once the spleens were placed in the cell culture dish, the splenocytes were removed by teasing the spleen and the resulting splenic cell suspension was placed in a 15 ml conical tube and large debris was allowed to settle for 2-3 minutes. At this time, the counted P3 cells were transferred to a 50 ml conical tube. In addition, the splenic-cell suspension was removed from the 15 ml conical tube, leaving behind the large debris and transferred to a new 15 ml conical tube. The splenic-cell suspension and the P3 cells were respectively pelleted by centrifugation.

Thereafter, the splenic cells (i.e., splenocytes) were washed with 10 ml of warm DMEM/HEPES, with gentle mixing to enable clots to stick to the pipet used to suspend the pelleted splenic cells. The P3 cells were also washed in 10 ml of DMEM/HEPES. The P3 cells and the splenic cells were again pelleted and respectively suspended in 5 ml each of warm DMEM/HEPES and mixed together in a 14 ml round-bottom tube (Falcon® 2059). The mixed-cell suspension was pelleted and the resulting supernatant was removed by aspiration. The resulting mixed-cell pellet was gently disrupted and incubated at 37° C. for 1-2 minutes.

In order to induce fusion of the splenic cells and P3 cells, 1 ml of 50% PEG/DMSO (Sigma) was added over 45-60 seconds with constant stirring and flicking. The cell suspension was then swirled at 37° C. for 45 seconds. After this incubation, the PEG was diluted out by adding 2 ml of warm DMEM/HEPES/5% DMSO over 2 minutes in the same manner as the PEG (i.e., stirring, flicking, and swirling at 37° C. After this addition, the mixture was further diluted by adding 8 ml of DMEM/HEPES/DMSO over 2 minutes and the fused cells were incubated for 15 minutes at 37° C. After the incubation, the fused cells were pelleted and suspended in 160 ml of fusion medium with freshly added Nutridoma. The resulting mixture was plated at 200 μl/well and incubated in a plastic container at 37° C.

Screening of Fused Cells

Primary Screen

Initially, two 384-well plates were coated with 25 µl per well of approximately 0.5 µg/ml of the protein of interest (e.g., native ING4 polypeptide or a fragment thereof) in coating buffer (50 mM Tris-Cl, pH 9.5). These two 384-well plates were incubated overnight at 4° C.

On the day of the screening, the coating comprising the protein of interest was removed and 50 µl per well of blocking buffer (1% BSA) was added and the plates were incubated for 30 min at 37° C. Thereafter, 25 µl from each well from the fusion plates was added and incubated for 1 hr at room temperature (RT). The wells were then washed three times with 50 µl/well of PBS-Tween (PBS-T). After the washing step, 25 µl of 1 µg/ml horseradish peroxidase-conjugated-GAM (an anti-mouse antibody of goat origin) Fc in PBS-T was added to each well and incubated for 1 hr at RT. Each well was then washed three times with 50 µl/well of PBS-T. After the washing step, 25 µl of OPD substrate (Pierce) with 0.1% hydrogen peroxide was added to each well and incubated for 15 min at RT. After incubation, 25 µl of STOP buffer (2 M sulfuric acid) was added to each well and the absorbance from each well was reach at 495 nM. Thereafter, the resulting data was analyzed using 384-well spreadsheet to determine which hybridomas produced antibodies that bind to the protein of interest.

Example 2

Experimental Methods

Recombinant ING4 Protein Purification for Antibody Generation

DNA fragments encoding the N-terminal (AA 5-147) (SEQ ID NO:2) or C-terminal (AA 173-249) (SEQ ID NO:3) portion of ING4 were PCR-amplified using the pMIG-ING4 construct (Kim et al. (2004) *Proc Natl Acad Sci U S A* 101: 16251-16256) as a template with primer pairs: 5'-ATG-TATTTGGAACATTATCTGGAC (SEQ ID NO:4) and 5'-CCCTTTGGAACGAGCACGAGC (SEQ ID NO:5), 5'-ATGCCCTCAGTGACCTTTGGC (SEQ ID NO:6) and 5'-TTTCTTCTTCCGTTCTTGGGA (SEQ ID NO:7). The DNA fragments were cloned into the pET21b bacterial expression vector (Novagen, Madison, Wis.) in the coding frame with a 6×HIS epitope-tag at the 3' end of each fragment using EcoRI and XhoI restriction enzymes (New England BioLabs, Ipswich, Mass.). The DNA constructs were used to transform BL21 *E. coli* (Promega Corporation, Madison, Wis.). Recombinant proteins were induced by adding 1 mM IPTG (Promega) and purified from cell lysate using a Ni-NTA column (Novagen).

Production of Monoclonal Antibodies to ING4

Monoclonal antibodies (mAbs) were generated as previously described (Azorsa et al. (1999) *Hybridoma* 18: 281-287) with the following modifications: Synthetic Peptide ING4-156 corresponding to the ING4 amino acids 156-178 (CAPKTAQKKLKLVRTSPEYGMPS) (SEQ ID NO:8) was synthesized by Sigma-Genosys (The Woodlands, Tex.) with an additional cysteine at the N-terminus. The peptide was coupled to KLH and ovalbumin using a maleamide conjugation kit (Pierce Thermo Fisher Scientific, Rockford, Ill.). Female Balb/c mice (6-8 weeks old) were injected with an emulsion of 100 µg of recombinant ING4 (SEQ ID NO:2 and SEQ ID NO:3) or KLH-conjugated peptide ING4-156 with complete Freud's adjuvant (Sigma-Aldrich, St. Louis, Mo.) by intraperitoneal injection 3 times at 2-week intervals, followed by injections of 75 µg of recombinant protein or peptide in PBS for three consecutive days. Splenocytes were isolated and fused to the myeloma cell line P3×63Ag8.653 using PEG:DMSO (50:5, % v, Sigma-Aldrich), as described above, Fused cells were seeded in 96-well plates in DMEM: NCTC-109 (90:10, % v, Invitrogen, Carlsbad, Calif.) media supplemented with 20% FBS (Invitrogen), 2 mM Glutamax I (Invitrogen), 25 mM Hepes, 1×HAT (Sigma-Aldrich), Penicillin/Streptomycin, and 0.5×Nutridoma-CS (Roche, Branchburg, N.J.). Hybridoma colonies were screened by ELISA and were subcloned twice by limiting-dilution. Tissue culture supernatants from 6 independent hybridoma clones containing anti-ING4 mAbs termed BTIM-1 to BTIM-6, were collected and stored with 0.02% sodium azide at 4° C.

Hybridomas expressing monoclonal antibodies that specifically bind to human ING4 protein, as described above and below, were deposited with the American Type Tissue Culture Collection (ATCC; 10801 University Blvd, Manassas Va., 20110-2209) patent depository as original deposits under the Budapest Treaty and were given the following ATCC Accession Nos: clone BTIM-2 (ATCC Patent Deposit Designation PTA-120605, deposited Sep. 27, 2013); clone BTIM-3 (ATCC Patent Deposit Designation PTA-120606, deposited Sep. 27, 2013); and clone BTIM-4 (ATCC Patent Deposit Designation PTA-120607, deposited Sep. 27, 2013).

Tissue Culture

The ING4 overexpression construct in the pMIG retroviral vector, pMIG-ING4, has been described previously (Kim et al, (2004) *Proc Natl Acad Sci U S A* 101: 16251-16256). The pMIG-ING4HA construct was generated by cloning the nucleotide sequence encoding the hemagglutanin (HA) epitope into the 3' end of ING4 via PCR. Cells were transfected with plasmids using Effectene (Qiagen, Valencia, Calif. ). MCF10A, T47D, and MCF7 cells containing the pMIG vector or pMIG-ING4 were generated using retroviral infection as described previously (Kim et al. (2004) *Proc Natl Acad Sci USA* 101: 16251-16256), followed by fluorescent activated sorting for green fluorescent protein-positive cells. Lentiviral particles containing a non-targeting shRNA construct (shNT) or ING4 knock-down construct (shING4) in the pLKO.1 vector (Sigma-Aldrich) were used to infect MCF10A cells. Cells containing shRNA constructs were selected in media containing 2 µg/ml puromycin (Sigma-Aldrich). The luciferase reporter plasmid, pGL4.32[luc2P/NF-κB/Hygro], was purchased from Promega Corporation. Cells containing pGL4.32[luc2P/NF-κB/Hygro] were selected in media containing 400 µg/ml hygromycin (Invitrogen). HEK293T cells were grown in DMEM containing 10% fetal bovine serum (FBS, Thermo-Fisher, Waltham, Mass.). T47D and MCF7 cells were grown in RPMI and MEM:EBSS media (Thermo-Fisher), respectively, supplemented with 10% FBS and 10 µg/ml bovine insulin (Sigma-Aldrich). MCF10A cells were grown in F10:DMEM media (Thermo-Fisher) supplemented with 10% FBS, 10 µg/ml bovine insulin, 10 ng/ml human epithelial growth factor (Invitrogen), and 1 µg/ml hydrocortisone (Sigma-Aldrich). Phorbol 12-myristate 13-acetate (PMA, Sigma-Aldrich) was dissolved in DMSO and used at a final concentration of 50 ng/ml.

Immunofluorescent Staining and Western Blot Analysis

MCF10A and T47D cells containing various constructs were plated on chamber slides to 50% confluency, fixed with 4% paraformaldehyde, and permeabilized with 0.1% Triton X-100. Cells were immunostained with an anti-ING4 antibody (BTIM-4, 1:10 dilution) and Rhodamine Red X-conjugated donkey anti-mouse secondary antibody (1:200, Jackson Immunoresearch, West Grove, Pa.). Cells were additionally stained for nuclei with 4',6-Diamidino-2-phenylindole (DAPI, Vector Labs, Burlingame, Calif.) and visualized using a fluorescent microscope. For Western blot analyses, anti-ING4 antibody was used in 1:10 dilution. Monoclonal antibodies for phospho-p65 (Ser536) (93H1) and p65/RelA (C22B4) and polyclonal antibodies for IκBα, IKKα, and IKKβ, were purchased from Cell Signaling and used at 1:1,000 dilutions. Anti-tubulin (DM1A, 1:2,000) and anti-histone H3 (1:1,000) monoclonal antibodies were purchased from Millipore (Billerica, Mass.).

Breast Tumor Tissue Microarray (TMA)

TMAs were constructed by extracting 0.6 mm diameter cores from the "donor" tumor tissue blocks and transferring tissue cores into a "recipient" paraffin block using an indexed manual arrayer, Tissue Arrayer VTA-100 (Veridiam Medical, El Cajon, Calif.) as previously described (Al-Kuraya et al. (2007) *J Clin Pathol* 60: 768-772). The TMAs contained 598 tissue punches from 249 independent tumor samples. Two-hundred thirty and 351 tissue spots on TMAs represented "double" and "triple punches" from 115 and 117 tissue samples, respectively. A common set of normal breast tissue controls was included on each TMA.

Immunohistochemistry (IHC)

Immunochemical staining of TMA sections was performed using BOND-MAX autostainer (Leics Microsystems, Germany). Antibodies used for IHC were anti-estrogen receptor-alpha (ER-α) monoclonal (1:200, Novocastra, Newcastle Upon Tyne, UK), anti-HER2/neu polyclonal (1:300, Novocastra), anti-phospho-p65 (Ser276) polyclonal (1:40, Cell Signaling, Danvers, Mass.), and anti-ING4 monoclonal (1:2, BTIM-4 cell culture supernatant). The staining intensity of estrogen receptor (ER) and HER2 was scored as described previously (Tapia et al. (2004) *Int J Oncol* 25: 1551-1557). All TMA and whole sections were scored manually by a board certified pathologist. An IHC score was assigned to each sample by averaging the scores of double or triple punch samples. The percent of evaluable IHC staining on TMAs ranged from 94.5% (ING4) to 99% (p-p65).

Binding Specificity Assays

The expression of full-length ING4 and fragments thereof, DC-1, DC-3, and DC-4, was provided using the pMIG retroviral vector, as described previously (Kim et al. (2004) *Proc Natl Acad Sci U S A* 101: 16251-16256). Fragment DC-1 corresponds to amino acids 1-180 (SEQ ID NO:10) of full-length ING4 protein. Fragment DC-3 corresponds to amino acids 67-180 (SEQ ID NO:11) of full-length ING4 protein. Fragment DC-4 corresponds to amino acids 126-249 (SEQ ID NO:12) of full-length ING4 protein. The pMIG constructs were generated by cloning the appropriate nucleotide sequences into the pMIG vector. Cells (HEK293T cells) were transiently transfected with plasmids using Effectene (Qiagen, Valencia, Calif.). 293T cells containing the pMIG vector with the respective constructs were grown in DMEM containing 10% fetal bovine serum (FBS, Thermo-Fisher, Waltham, Mass.). For Western Blot analysis, cells were lysed and the resulting lysate was probed using BTIM-1, BTIM-2, BTIM-4, BTIM-5, and BTIM-6 anti-ING4 antibodies in a 1:10 dilution.

Statistical Analysis

Relationship between tumor pathologic features and molecular markers or between molecular markers was analyzed using Fisher's Exact test. A dot plot was used to graph gene expression levels in each tumor. An unpaired 2-tailed student t-test was used to determine statistical significance. P-values <0.05 were considered statistically significant.

Example 3

Generation and Screening of Monoclonal ING4 Antibodies

Figure 2:
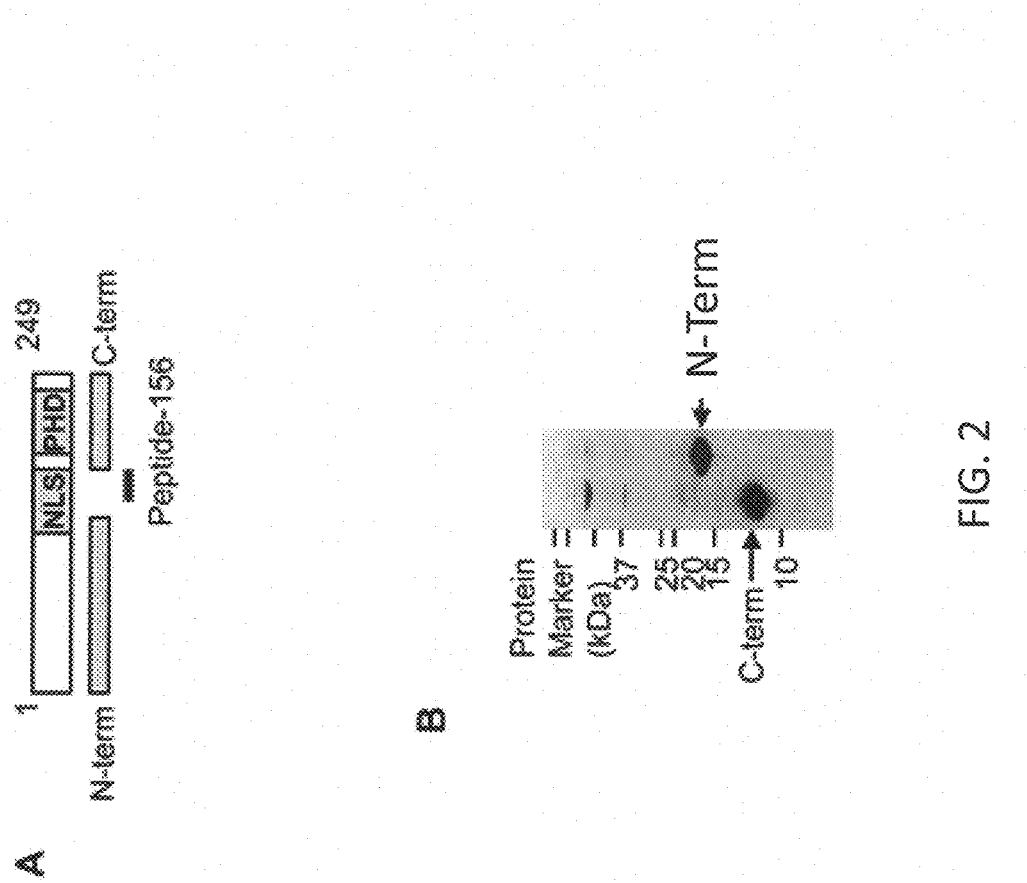
FIG. 2A is a schematic diagram of ING4 protein containing a nuclear localization signal (NLS) and a plant homeodomain (PHD). Stick figures represent the ING4 fragments that were used to immunize mice.
FIG. 2B shows the N-terminal (amino acids 5-147) and C-terminal (amino acids 173-249) recombinant fragments of ING4 purified from bacteria visualized by SDS-PAGE gel stained with Coomassie Blue.
Figure 3:
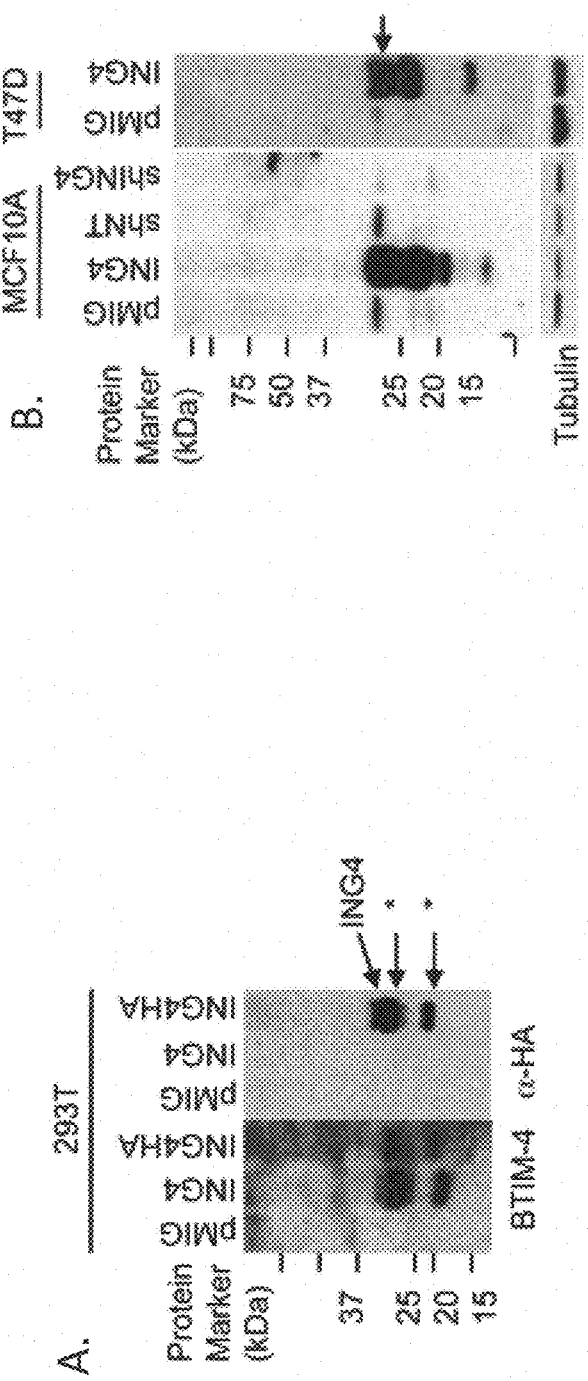
FIG. 3A shows the detection of ING4 and hemagglutanin (HA) epitope tagged ING4 overexpressed in 293T cells by Western blot using BTIM-4 and anti-HA monoclonal antibody. * denotes smaller ING4-derived protein species recognized by the antibody.
FIG. 3B is a Western blot analysis of ING4 protein expression using BTIM-4 antibody in MCF10A breast epithelial cells and T47D breast cancer cells containing pMIG (the vector control), ING4 (ING4 overexpression), shNT (non-targeting short hairpin RNA (shRNA) control), or shING4 (shRNA targeting ING4). Tubulin antibody was used as a loading control.

In order to evaluate ING4 protein expression in breast tumors, a monoclonal antibody was generated that specifically binds to ING4 protein. Mice were immunized with N-terminal (AA 5-147) (SEQ ID NO:2) or C-terminal (AA 173-249) (SEQ ID NO:3) recombinant ING4 protein fragments produced in bacteria and also with Synthetic Peptide corresponding to amino acids 156-178 of ING4 (SEQ ID NO:8) (see FIGS. 2A and 2B). The N-terminal ING4 protein injection generated antibodies that recognized ING4 with specificity, one of which was designated BTIM-4, The BTIM-4 antibody detected full-length ING4 protein and ING4 epitope-tagged with hemagglutinin (HA) at the C-terminal end, which was overexpressed in 293T cells (FIG. 3A). Both BTIM-4 and anti-HA antibodies detected additional ~26 kDa and 17 kDa species which may represent degradation products of overexpressed ING4 (asterisks in FIG. 3A). BTIM-4 antibody did not cross-react with the other ING family member proteins, ING1, ING2, or ING5, which were all overexpressed in 293T cells, but did detect the mouse ING4 protein that shares 99% amino acid identity with the human ING4 protein (data not shown). The C-terminal ING4 protein injection failed to produce antibody that specifically binds to ING4 (data not shown), possibly due to the fact that the C-terminal fragment contains the PHD finger motif conserved among the ING family members and other transcription factors. The injection of Synthetic Peptide of SEQ ID NO:8 generated antibodies that recognized overexpressed ING4 but with high background non-specific bands (data not shown). The BTIM-4 antibody was characterized further and is herein referred to as anti-ING4 antibody.

Next, testing was conducted to determine whether anti-ING4 antibody detected endogenous ING4 protein in MCF10A and T47D cells by Western blot. MCF10A cells are a normal immortalized breast epithelial cell line with two copies of the ING4 gene. T47D cells are a breast cancer cell line that contains only one copy of the ING4 gene due to a defined deletion on chromosome 12, providing an example of "ING4 low" expressing cells. Consistent with this, T47D cells contained 10-fold less ING4 transcript compared to MCF10A cells, normalized to the amount of GAPDH transcript in each cell line (data not shown). The Western blot analysis of the cell lines showed that the anti-ING4 antibody detected a range of ING4 protein expression levels reflective of the relative mRNA expression in each cell line (FIG. 3B).

Figure 4:
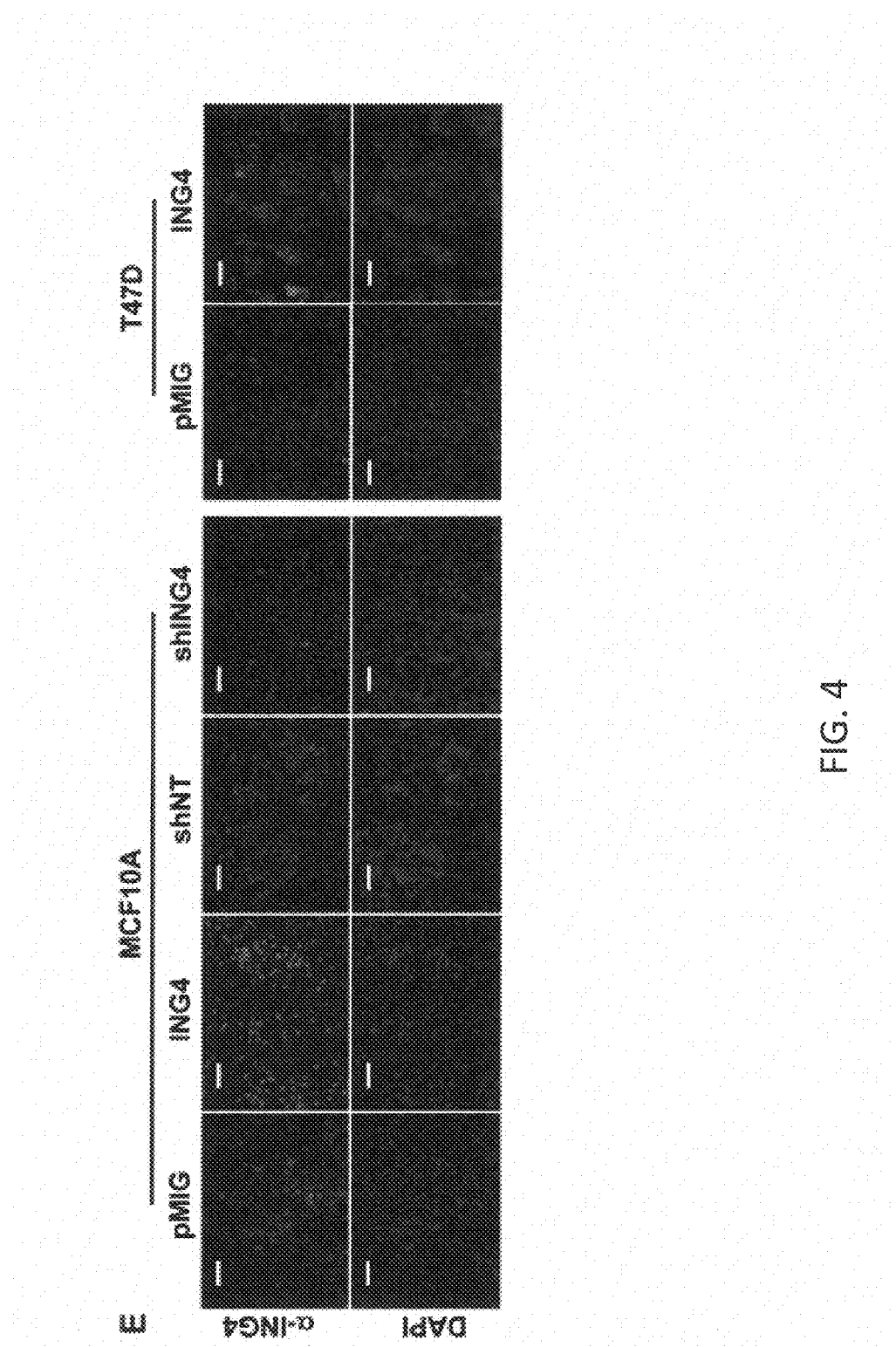
FIG. 4 presents MCF10A cells transduced with pMIG (the vector control), ING4 (ING4 overexpression), shNT (non-targeting shRNA control), or shING4 (shRNA targeting ING4), and T47D cells transduced with pMIG (the vector control) or ING4 (ING4 overexpression) were immunostained with BTIM-4 anti-ING4 antibody and visualized using fluorescent microscopy. 4',6-Diamidino-2-phenylindole (DAPI) was used to stain individual cell nuclei. White scale bars represent 100 µm.

Next, immunofluorescent staining of ING4 was performed in the MCF10A and T47D cell lines using the anti-ING4 antibody. The results showed nuclear and cytosolic staining of ING4 in both MCF10A and T47D vector control cells, indicating the antibody could detect endogenous levels of ING4 (FIG. 4). MCF10A and T47D cells overexpressing ING4 showed increased nuclear staining of ING4, compared to their respective vector control cells, whereas MCF10A cells with the ING4 knock-down construct showed diminished ING4 staining compared to the shNT control (FIG. 4). We also increased the photographic exposure time for the T47D cell images in order to visualize the endogenous ING4 protein staining in T47D-pMIG cells, and compared it to the overexpressed ING4 protein staining in T47D-ING4 cells (data not shown). These results supported the sensitivity of the anti-ING4 antibody in detecting different amounts of the ING4 protein.

Example 4

Figure 5:
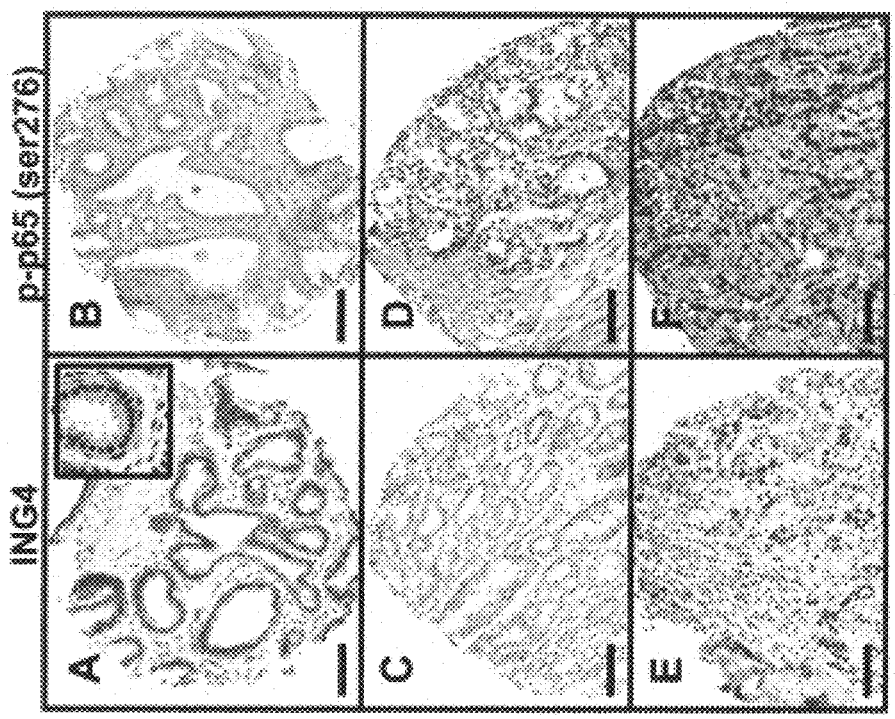
FIGS. 5A and 5B show hyperplastic breast tissue with moderate atypia from a ductal carcinoma in situ case, showing ING4 score +3 and p-p65 score 0. Inset is a higher magnification image of the region showing ING4 staining in luminal and basal epithelial cells and in stroma cells.
FIGS. 5C and 5D present invasive ductal carcinoma with ING4 score 0 and p-p65 score +2.
FIGS. 5E and 5F show grade 3 invasive ductal carcinoma with ING4 score +1 and p-p65 score +3. (bars, 100 µm).

ING4 Immunohistochemical Staining of Breast Tumor Samples and Correlation with Tumor Features Experiments were performed to evaluate ING4 protein expression using the anti-ING4 antibody in breast tumor samples using immunohistochemistry on tumor tissue microarrays (TMAs). Nuclear staining of ING4 in tumor samples was scored on a scale of 0 to +3: intense and uniform nuclear staining was assigned +3 (FIG. 5A) and no staining was assigned 0 (FIG. 5C). A normal to slightly hyperplastic breast tissue section taken from a ductal carcinoma in situ (DCIS)-only case showed distinct nuclear ING4 staining in both luminal epithelial and myoepithelial cells within the ductal structure (FIG. 5A inset). Stromal cells also stained for nuclear ING4 but with less intensity compared to epithelial cells. Normal breast tissue sections showed identical staining pattern and intensity for ING4 as the section sample shown in FIG. 5A (data not shown).

An ING4 IHC score was assigned for each tumor sample by averaging the scores between "double" and "triple punches" on TMAs and defined less than 1.5 (<1.5) scores as "low ING4" and greater than or equal to 1.5 (≥1.5) scores as "high ING4." It was observed that 77 tumors among 227 tumors scored <1.5, constituting 34% of tumor samples that expressed low levels of ING4 (Table 1). ING4 IHC scores were then correlated with pathologic features including histologic subtype, tumor size, BRE grade, and lymph node status (see Table 1). All 6 DCIS cases showed +3 score for ING4 (Table 1), indicating that this non-invasive form of breast cancer expressed ING4 at a level that is detectable by IHC using the anti-ING4 antibody. ING4-low tumors were comparably prevalent between invasive ductal carcinoma and lobular carcinoma (32% vs 30%; Table 1), suggesting a tumor suppressive role of ING4 in breast cancers arising from both ductal and lobular structures. Low ING4 expression was more frequently found in tumors that were large in size (≥2 cm in diameter, 41%), high grade (grade 2 and 3, 40-41%), and lymph node-positive (51%, Table 1; see bold font). Although statistical significance could not be assigned due to the small cohort size, these data show a consistent trend that more advanced breast tumors expressed lower levels of ING4. As such, down-regulation or a loss of ING4 protein expression may contribute to breast cancer progression.

TABLE 1

Tumors with low ING4 protein staining frequently have advanced tumor features.

| Pathologic Feature | Subcategory | ING4 Score <1.5 | ING4 Score ≥1.5 | P value |
|---|---|---|---|---|
| | | 77 (34%) | 150 (66%) | |
| Histologic Subtype | Ductal cell carcinoma in situ | 0 | 6 (100%) | — |
| | Invasive ductal carcinoma | 51 (32%) | 108 (68%) | 1 |
| | Invasive lobular carcinoma | 6 (30%) | 14 (70%) | 0.207 |
| Size (diameter) | <2.0 cm | 8 (28%) | 21 (72%) | |
| | ≥2.0 cm | 47 (41%) | 68 (59%) | |
| Bloom, Richardson, Elston-Ellis (BRE) Grading | Grade 1 | 8 (27%) | 20 (71%) | 0.284 |
| | Grade 2 | 29 (40%) | 43 (60%) | |
| | Grade 3 | 17 (41%) | 25 (59%) | |
| Lymph node status | N0 | 23 (35%) | 43 (65%) | 0.143 |
| | >N0 | 19 (51%) | 18 (49%) | |

Example 5

Low ING4 Expression Correlates with High Levels of Phosphorylated p65/RelA in Breast Tumors Next, it was determined that ING4 protein expression correlated with the molecular subtype markers, Estrogen Receptor (ER) and HER2. ING4-low tumors were equally prevalent between ER+ and ER-negative tumors (35% ER+ vs. 29% ER-negative, FIG. 6), as was the case between HER2+ vs. HER2-negative tumors (33% HER2+ vs 34% HER2-negative, FIG. 6). In addition, an increased frequency of ING4-low tumors was not observed in any of the four molecular subtypes (luminal A, luminal B, basal-like, and HERZ data not shown).

Next, it was tested whether low ING4 expression correlated with NF-κB activation in breast tumors by staining the TMAs with an antibody against the p65/RelA subunit phosphorylated at the amino acid residue serine 276 (p-p65/RelA), which is an activated form of NF-κB. Neither normal breast tissue nor the six DCIS samples showed nuclear p-p65/RelA IHC staining, suggesting that p-p65-high represents aberrant NF-κB activation in breast cancer (data not shown).

Figure 6:
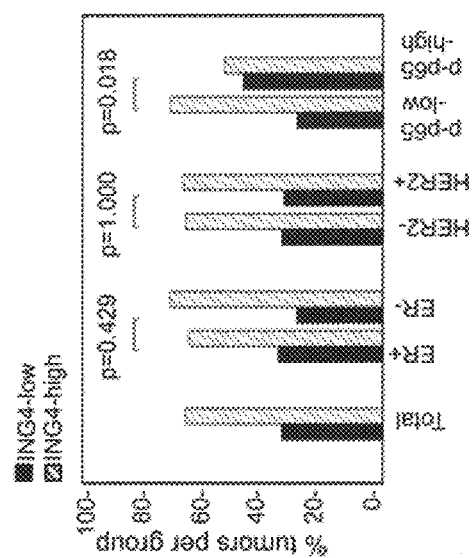
FIG. 6 depicts how low ING4 expression is more prevalent in the tumors that express high levels of p-p65. Number of ING4-low (solid bars, IHC score <1.5) and ING4-high (slanted-line bars, IHC score≥1.5) tumors, presented as a percentage of total number of tumors in each subgroup. Total (n=227, 77 ING4-low, 150 ING4-high), ER+ (n=156, 55 ING4-low, 101 ING4-high), ER−(n=63, 18 ING4-low, 45 ING4-high), HER2− (n=197, 67 ING4-low, 130 ING4-high), HER2+ (n=27, 9 ING4-low, 18 ING4-high), p-p65-low (n=166, 48 ING4-low, 118 ING4-high), and p-p65-high (n=62, 29 ING4-low, 33 ING4-high). P values were determined by Fisher's Exact test.

Nuclear p-p65/RelA staining was scored on a scale of 0 to +3 (FIGS. 5B, 5D, 5F), the scores were averaged between double and triple punches of each sample, and the average scores were defined <1.5 scores as "p-p65-low" and ≥1.5 scores as "p-p65-high." The relationship between p-p65/RelA and ING4 expression was then evaluated in breast tumor samples and found that 47% of p-p65-high tumors expressed low levels of ING4 protein, compared to 29% of p-p65-low tumors (p=0.018, FIG. 6). Two examples of the tumors that showed low ING4 and high p-p65 protein levels are shown in FIGS. 5C-5F. These data indicate a statistically significant correlation between low ING4 protein levels and high p-p65 protein levels. Furthermore, it was also noted that ING4-low/p-p65-high tumors were more frequently lymph node-positive (57%), compared to tumors with the other expression level makeups (27-39%, Table 2). These results suggest that phospho-activation of NF-κB may contribute to the high metastatic tendency of ING4-low tumors. Down-regulation of ING4 may foster phospho-activation of p65/RelA, resulting in aggressive breast cancer.

TABLE 2

Tumors with low ING4 and high p-p65 levels are frequently lymph node-positive.

| Markers | Subcategories | Lymph Node Negative | Lymph Node Positive |
|---|---|---|---|
| (n = 103) | | 66 (64%) | 37 (36%) |
| ING4 score <1.5 | p-p65 < 1.5 (n = 28) | 17 (61%) | 11 (39%) |
| | p-p65 ≥ 1.5 (n = 14) | 6 (43%) | 8 (57%) |
| ING4 score ≥1.5 | p-p65 < 1.5 (n = 50) | 35 (70%) | 15 (30%) |
| | p-p65 ≥ 1.5 (n = 11) | 8 (73%) | 3 (27%) |

Example 6

Binding Specificity of Monoclonal Antibodies

Figure 7:
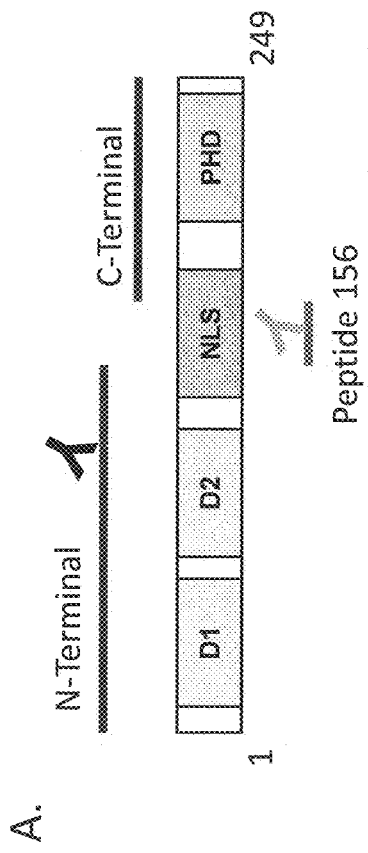
FIG. 7A is a schematic diagram of ING4 protein containing Domain 1, Domain 2, the NLS, and the PHD. Stick figures represent the ING4 fragments that were used to immunize mice and illustrated antibodies ("Y") represent antibodies generated using the respective ING4 fragments.
FIG. 7B is a schematic representing the results of a binding assay conducted to assess binding location of the antibodies generated using the ING4 fragments.
Figure 7:
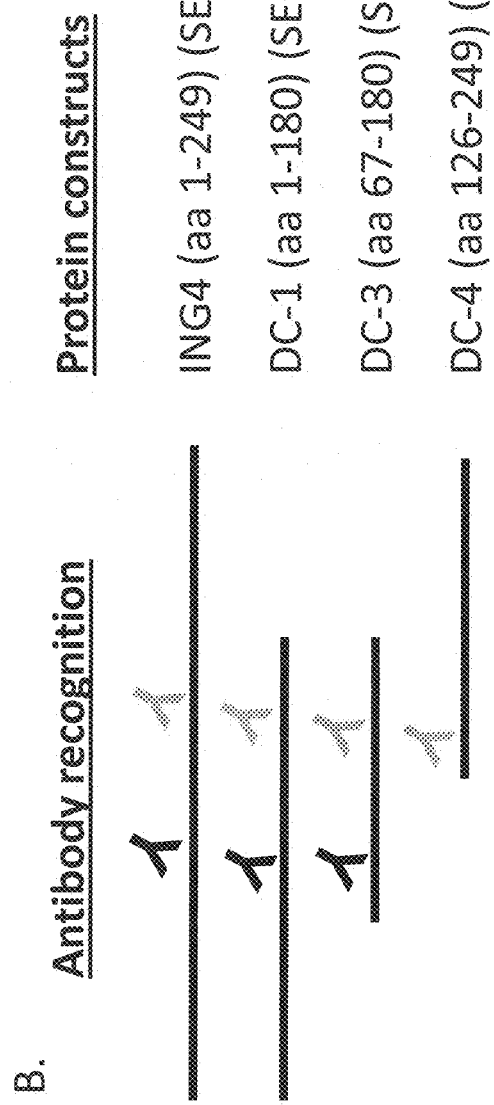

Next, binding assays were performed to assess to which domains the anti-ING4 antibodies specifically bind. As illustrated in FIG. 7A, ING4 protein comprises four domains, Domain 1, Domain 2, the NLS, and the PHD. In particular, Domain 1 (D1 in FIG. 7A), which exhibits a leucine-zipper like configuration, is generally adjacent to the N-terminus of ING4. Domain 2 (D2 in FIG. 7A), which exhibits a lamin binding domain-like configuration, extends from amino acids 68-119 (SEQ ID NO:9).

In order to elucidate the regions of ING4 where the respective anti-ING4 antibodies bind, Western blot-based binding assays were performed with truncated forms of ING4. As illustrated in FIG. 7B, four different polypeptides were used to assess binding specificity. Full-length ING4 (SEQ ID NO:1) was used as a positive control and the following truncation constructs were also used: DC-1, which comprises amino acids 1-180 of ING4 (SEQ ID NO:10), DC-3, which comprises amino acids 67-180 of ING4 (SEQ ID NO:11), and DC-4, which comprises amino acids 126-249 of ING4 (SEQ ID NO:12). Moreover, the binding specificity of the anti-ING4 antibodies generated with the N-terminal amino acids 5-147 (SEQ ID NO:2) (BTIM-1, BTIM-2, and BTIM-4) were compared to the binding specificity of the anti-ING4 antibodies generated with the Synthetic Peptide (SEQ ID NO:8) (BTIM-5 and BTIM-6). It was found that all of the anti-ING4 antibodies tested in these experiments bound to ING4, DC-1, and DC-3. Moreover, it was also noted that none of BTIM-1, BTIM-2, or BTIM-4 bound to DC-4. As such, these results suggest that BTIM-5 and BTIM-6 bind to ING4 at one or more positions between amino acids 126 and 249 and do not exhibit significant binding to ING4 protein between amino acids 1 and 125.

Moreover, these results further suggest that BTIM-1, BTIM-2, and BTIM-4 specifically bind to ING4 at one or more positions within Domain 2 (SEQ ID NO:9). Particularly, BTIM-1, BTIM-2, and BTIM-4 each bound to the native ING4 polypeptide of SEQ ID NO:1 as well as amino acids 1-180 (DC-1) and 67-180 (DC-3). However, binding of BTIM-1, BTIM-2, and BTIM-4 was abrogated in the DC-4 group, which lacks Domain 2. In addition, BTIM-1, BTIM-2, and BTIM-4 also specifically bound to DC-3, which lacks Domain 1. As such, these results indicate that BTIM-1, BTIM-2, and BTIM-4 each specifically bind to one or more positions within Domain 2 (SEQ ID NO:9), which is encompassed within the N-terminal amino acids of SEQ ID NO:2.

Having herein set forth the various embodiments of the present invention, it is anticipated that suitable modifications can be made thereto which will nonetheless remain within the scope of the invention. The invention shall therefore only be construed in accordance with the following claims below.

What is claimed is:

1. A monoclonal antibody that is capable of specifically binding to human ING4, wherein the antibody is selected from the group consisting of:
   (a) a monoclonal antibody produced by the hybridoma cell line BTIM-2, deposited with the ATCC as Patent Deposit No. PTA 120605;
   (b) a monoclonal antibody produced by the hybridoma cell line BTIM-3, deposited with the ATCC as Patent Deposit No. PTA 120606; and
   (c) a monoclonal antibody produced by the hybridoma cell line BTIM-4, deposited with the ATCC as Patent Deposit No. PTA 120607.

2. The monoclonal antibody of claim 1, wherein the antibody is an IgG1, kappa chain isotype.

3. A monoclonal antibody produced by hybridoma cell line BTIM-4, ATCC accession number PTA 120607.

4. A method comprising the steps of:
   (a) reacting an anti-ING4 monoclonal antibody with a sample collected from a subject, wherein the sample is at least one sample selected from the group consisting of a tissue sample, a blood sample, a serum sample, a plasma sample, and bodily fluid, wherein the anti-ING4 monoclonal antibody has the same epitope specificity as a monoclonal antibody produced by hybridoma cell line BTIM-4, ATCC accession number PTA 120607;
   (b) detecting a level of ING4 protein in the sample.

5. The method according to claim 4, wherein the anti-ING4 antibody is labeled.

6. The method according to claim 5, wherein the anti-ING4 antibody is labeled with one or more labels selected from the group consisting of a biotin label, a fluorescent label, an enzyme label, a coenzyme label, a chemiluminescent label, and a radioactive isotope label.

7. The method of claim 4, further comprising the steps of:
   (d) reacting an anti-p-p65/ReIA antibody with the sample;
   (e) detecting a level of p-p65/ReIA protein in the sample.

* * * * *

SEQUENCE LISTING

<160> NUMBER OF SEQ ID NOS: 12

<210> SEQ ID NO 1
<211> LENGTH: 249
<212> TYPE: PRT
<213> ORGANISM: Homo sapiens

<400> SEQUENCE: 1

```
Met Ala Ala Gly Met Tyr Leu Glu His Tyr Leu Asp Ser Ile Glu Asn
1               5                   10                  15

Leu Pro Phe Glu Leu Gln Arg Asn Phe Gln Leu Met Arg Asp Leu Asp
            20                  25                  30

Gln Arg Thr Glu Asp Leu Lys Ala Glu Ile Asp Lys Leu Ala Thr Glu
        35                  40                  45

Tyr Met Ser Ser Ala Arg Ser Leu Ser Ser Glu Glu Lys Leu Ala Leu
    50                  55                  60

Leu Lys Gln Ile Gln Glu Ala Tyr Gly Lys Cys Lys Glu Phe Gly Asp
65                  70                  75                  80

Asp Lys Val Gln Leu Ala Met Gln Thr Tyr Glu Met Val Asp Lys His
                85                  90                  95

Ile Arg Arg Leu Asp Thr Asp Leu Ala Arg Phe Glu Ala Asp Leu Lys
            100                 105                 110

Glu Lys Gln Ile Glu Ser Ser Asp Tyr Asp Ser Ser Ser Ser Lys Gly
        115                 120                 125

Lys Lys Lys Gly Arg Thr Gln Lys Glu Lys Lys Ala Ala Arg Ala Arg
    130                 135                 140

Ser Lys Gly Lys Asn Ser Asp Glu Glu Ala Pro Lys Thr Ala Gln Lys
145                 150                 155                 160

Lys Leu Lys Leu Val Arg Thr Ser Pro Glu Tyr Gly Met Pro Ser Val
                165                 170                 175

Thr Phe Gly Ser Val His Pro Ser Asp Val Leu Asp Met Pro Val Asp
            180                 185                 190

Pro Asn Glu Pro Thr Tyr Cys Leu Cys His Gln Val Ser Tyr Gly Glu
        195                 200                 205
```

```
Met Ile Gly Cys Asp Asn Pro Asp Cys Ser Ile Glu Trp Phe His Phe
    210                 215                 220

Ala Cys Val Gly Leu Thr Thr Lys Pro Arg Gly Lys Trp Phe Cys Pro
225                 230                 235                 240

Arg Cys Ser Gln Glu Arg Lys Lys Lys
                245

<210> SEQ ID NO 2
<211> LENGTH: 143
<212> TYPE: PRT
<213> ORGANISM: Artificial Sequence
<220> FEATURE:
<223> OTHER INFORMATION: Amino acids 5-147 of ING4 Protein

<400> SEQUENCE: 2

Met Tyr Leu Glu His Tyr Leu Asp Ser Ile Glu Asn Leu Pro Phe Glu
1               5                   10                  15

Leu Gln Arg Asn Phe Gln Leu Met Arg Asp Leu Asp Gln Arg Thr Glu
                20                  25                  30

Asp Leu Lys Ala Glu Ile Asp Lys Leu Ala Thr Glu Tyr Met Ser Ser
            35                  40                  45

Ala Arg Ser Leu Ser Ser Glu Glu Lys Leu Ala Leu Leu Lys Gln Ile
50                  55                  60

Gln Glu Ala Tyr Gly Lys Cys Lys Glu Phe Gly Asp Lys Val Gln
65                  70                  75                  80

Leu Ala Met Gln Thr Tyr Glu Met Val Asp Lys His Ile Arg Arg Leu
                85                  90                  95

Asp Thr Asp Leu Ala Arg Phe Glu Ala Asp Leu Lys Glu Lys Gln Ile
            100                 105                 110

Glu Ser Ser Asp Tyr Asp Ser Ser Ser Lys Gly Lys Lys Gly
        115                 120                 125

Arg Thr Gln Lys Glu Lys Lys Ala Ala Arg Ala Arg Ser Lys Gly
    130                 135                 140

<210> SEQ ID NO 3
<211> LENGTH: 77
<212> TYPE: PRT
<213> ORGANISM: Artificial Sequence
<220> FEATURE:
<223> OTHER INFORMATION: C Terminal Amino Acids 173-249 of ING4

<400> SEQUENCE: 3

Met Pro Ser Val Thr Phe Gly Ser Val His Pro Ser Asp Val Leu Asp
1               5                   10                  15

Met Pro Val Asp Pro Asn Glu Pro Thr Tyr Cys Leu Cys His Gln Val
                20                  25                  30

Ser Tyr Gly Glu Met Ile Gly Cys Asp Asn Pro Asp Cys Ser Ile Glu
            35                  40                  45

Trp Phe His Phe Ala Cys Val Gly Leu Thr Thr Lys Pro Arg Gly Lys
50                  55                  60

Trp Phe Cys Pro Arg Cys Ser Gln Glu Arg Lys Lys Lys
65                  70                  75

<210> SEQ ID NO 4
<211> LENGTH: 24
<212> TYPE: DNA
<213> ORGANISM: Artificial Sequence
<220> FEATURE:
<223> OTHER INFORMATION: Primer 1
```

-continued

```
<400> SEQUENCE: 4
atgtatttgg aacattatct ggac                                            24

<210> SEQ ID NO 5
<211> LENGTH: 21
<212> TYPE: DNA
<213> ORGANISM: Artificial Sequence
<220> FEATURE:
<223> OTHER INFORMATION: Primer 2

<400> SEQUENCE: 5
ccctttggaa cgagcacgag c                                               21

<210> SEQ ID NO 6
<211> LENGTH: 21
<212> TYPE: DNA
<213> ORGANISM: Artificial Sequence
<220> FEATURE:
<223> OTHER INFORMATION: Primer 3

<400> SEQUENCE: 6
atgccctcag tgacctttgg c                                               21

<210> SEQ ID NO 7
<211> LENGTH: 21
<212> TYPE: DNA
<213> ORGANISM: Artificial Sequence
<220> FEATURE:
<223> OTHER INFORMATION: Primer 4

<400> SEQUENCE: 7
tttcttcttc cgttcttggg a                                               21

<210> SEQ ID NO 8
<211> LENGTH: 23
<212> TYPE: PRT
<213> ORGANISM: Artificial Sequence
<220> FEATURE:
<223> OTHER INFORMATION: Amino Acids 156-178 of ING4

<400> SEQUENCE: 8

Cys Ala Pro Lys Thr Ala Gln Lys Lys Leu Lys Leu Val Arg Thr Ser
1               5                   10                  15

Pro Glu Tyr Gly Met Pro Ser
            20

<210> SEQ ID NO 9
<211> LENGTH: 52
<212> TYPE: PRT
<213> ORGANISM: Artificial Sequence
<220> FEATURE:
<223> OTHER INFORMATION: Amino Acids 68-119 of ING4

<400> SEQUENCE: 9

Ile Gln Glu Ala Tyr Gly Lys Cys Lys Glu Phe Gly Asp Asp Lys Val
1               5                   10                  15

Gln Leu Ala Met Gln Thr Tyr Glu Met Val Asp Lys His Ile Arg Arg
            20                  25                  30

Leu Asp Thr Asp Leu Ala Arg Phe Glu Ala Asp Leu Lys Glu Lys Gln
        35                  40                  45

Ile Glu Ser Ser
    50
```

```
<210> SEQ ID NO 10
<211> LENGTH: 180
<212> TYPE: PRT
<213> ORGANISM: Artificial Sequence
<220> FEATURE:
<223> OTHER INFORMATION: Amino Acids 1-180 of ING4

<400> SEQUENCE: 10

Met Ala Ala Gly Met Tyr Leu Glu His Tyr Leu Asp Ser Ile Glu Asn
1               5                   10                  15

Leu Pro Phe Glu Leu Gln Arg Asn Phe Gln Leu Met Arg Asp Leu Asp
            20                  25                  30

Gln Arg Thr Glu Asp Leu Lys Ala Glu Ile Asp Lys Leu Ala Thr Glu
        35                  40                  45

Tyr Met Ser Ser Ala Arg Ser Leu Ser Glu Glu Lys Leu Ala Leu
    50                  55                  60

Leu Lys Gln Ile Gln Glu Ala Tyr Gly Lys Cys Lys Glu Phe Gly Asp
65                  70                  75                  80

Asp Lys Val Gln Leu Ala Met Gln Thr Tyr Glu Met Val Asp Lys His
                85                  90                  95

Ile Arg Arg Leu Asp Thr Asp Leu Ala Arg Phe Glu Ala Asp Leu Lys
            100                 105                 110

Glu Lys Gln Ile Glu Ser Ser Asp Tyr Asp Ser Ser Ser Lys Gly
        115                 120                 125

Lys Lys Lys Gly Arg Thr Gln Lys Glu Lys Lys Ala Ala Arg Ala Arg
130                 135                 140

Ser Lys Gly Lys Asn Ser Asp Glu Glu Ala Pro Lys Thr Ala Gln Lys
145                 150                 155                 160

Lys Leu Lys Leu Val Arg Thr Ser Pro Glu Tyr Gly Met Pro Ser Val
                165                 170                 175

Thr Phe Gly Ser
            180

<210> SEQ ID NO 11
<211> LENGTH: 114
<212> TYPE: PRT
<213> ORGANISM: Artificial Sequence
<220> FEATURE:
<223> OTHER INFORMATION: Amino Acids 67-180 of ING4

<400> SEQUENCE: 11

Gln Ile Gln Glu Ala Tyr Gly Lys Cys Lys Glu Phe Gly Asp Asp Lys
1               5                   10                  15

Val Gln Leu Ala Met Gln Thr Tyr Glu Met Val Asp Lys His Ile Arg
            20                  25                  30

Arg Leu Asp Thr Asp Leu Ala Arg Phe Glu Ala Asp Leu Lys Glu Lys
        35                  40                  45

Gln Ile Glu Ser Ser Asp Tyr Asp Ser Ser Ser Lys Gly Lys Lys
    50                  55                  60

Lys Gly Arg Thr Gln Lys Glu Lys Lys Ala Ala Arg Ala Arg Ser Lys
65                  70                  75                  80

Gly Lys Asn Ser Asp Glu Glu Ala Pro Lys Thr Ala Gln Lys Lys Leu
                85                  90                  95

Lys Leu Val Arg Thr Ser Pro Glu Tyr Gly Met Pro Ser Val Thr Phe
            100                 105                 110

Gly Ser
```

```
<210> SEQ ID NO 12
<211> LENGTH: 124
<212> TYPE: PRT
<213> ORGANISM: Artificial Sequence
<220> FEATURE:
<223> OTHER INFORMATION: Amino Acids 126-249 of ING4

<400> SEQUENCE: 12

Ser Lys Gly Lys Lys Gly Arg Thr Gln Lys Glu Lys Lys Ala Ala
1               5                   10                  15

Arg Ala Arg Ser Lys Gly Lys Asn Ser Asp Glu Glu Ala Pro Lys Thr
            20                  25                  30

Ala Gln Lys Lys Leu Lys Leu Val Arg Thr Ser Pro Glu Tyr Gly Met
        35                  40                  45

Pro Ser Val Thr Phe Gly Ser Val His Pro Ser Asp Val Leu Asp Met
        50                  55                  60

Pro Val Asp Pro Asn Glu Pro Thr Tyr Cys Leu Cys His Gln Val Ser
65                  70                  75                  80

Tyr Gly Glu Met Ile Gly Cys Asp Asn Pro Asp Cys Ser Ile Glu Trp
                85                  90                  95

Phe His Phe Ala Cys Val Gly Leu Thr Thr Lys Pro Arg Gly Lys Trp
            100                 105                 110

Phe Cys Pro Arg Cys Ser Gln Glu Arg Lys Lys Lys
            115                 120
```